(12) United States Patent
Tsuboyama et al.

(10) Patent No.: US 6,991,857 B2
(45) Date of Patent: Jan. 31, 2006

(54) METAL COORDINATION COMPOUND, LUMINESCENCE DEVICE AND DISPLAY APPARATUS

(75) Inventors: Akira Tsuboyama, Sagamihara (JP); Hidemasa Mizutani, Sagamihara (JP); Shinjiro Okada, Isehara (JP); Takao Takiguchi, Tokyo (JP); Seishi Miura, Sagamihara (JP); Koji Noguchi, Sagamihara (JP); Takashi Moriyama, Kawasaki (JP); Satoshi Igawa, Fujisawa (JP); Jun Kamatani, Kawasaki (JP); Manabu Furugori, Atsugi (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 09/995,608

(22) Filed: Nov. 29, 2001

(65) Prior Publication Data
US 2003/0054198 A1    Mar. 20, 2003

(30) Foreign Application Priority Data

| Dec. 1, 2000 | (JP) | ............................. 2000-367080 |
| Jun. 29, 2001 | (JP) | ............................. 2001-198439 |
| Nov. 20, 2001 | (JP) | ............................. 2001-354703 |

(51) Int. Cl.
  *H05B 33/14* (2006.01)
  *C09K 11/06* (2006.01)

(52) U.S. Cl. .................. 428/690; 428/917; 313/504; 313/506; 546/4

(58) Field of Classification Search ................ 428/690, 428/917; 313/504, 506; 257/40, 102, 103; 252/301.16; 546/4, 6, 10; 549/3
See application file for complete search history.

(56) References Cited

U.S. PATENT DOCUMENTS

| 5,698,858 | A | 12/1997 | Börner et al. ............ 250/484.2 |
| 5,756,224 | A | 5/1998 | Börner et al. ............... 428/690 |
| 2001/0019782 | A1 * | 9/2001 | Igarashi et al. ............. 428/690 |
| 2002/0024293 | A1 * | 2/2002 | Igarashi et al. ............. 313/483 |
| 2002/0034656 | A1 * | 3/2002 | Thompson et al. ......... 428/690 |

(Continued)

FOREIGN PATENT DOCUMENTS

EP         1 191 612 A2        3/2002

(Continued)

OTHER PUBLICATIONS

Maestri et al., "Photochemistry and Luninescence of Cycometallated Complexes", Advances in Photochemistry, vol. 17, 1992, pp. 1-68 (no month).*

(Continued)

Primary Examiner—Marie Yamnitzky
(74) Attorney, Agent, or Firm—Fitzpatrick, Cella, Harper & Scinto

(57) ABSTRACT

An organic EL device includes a luminescence layer containing, as a luminescent material allowing a high-luminescence and high-efficiency luminescence for a long period of time, a metal coordination compound represented by the following formula (1): LmML'n, wherein M denotes Ir, Pt, Rh or Pd; L denotes a bidentate ligand; L' denotes a bidentate ligand different from L; m is an integer of 1, 2 or 3; and n is an integer of 0, 1 or 2 with the proviso that the sum of m and n is 2 or 3. The partial structure MLm is represented by a formula (2) or a formula (3) shown below, and the partial structure ML'n is represented by a formula (4) or a formula (5) shown below:

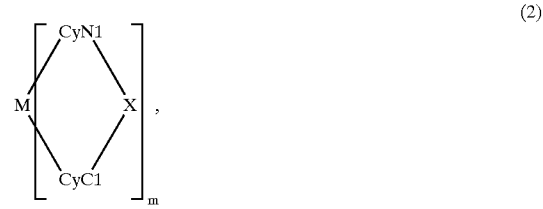

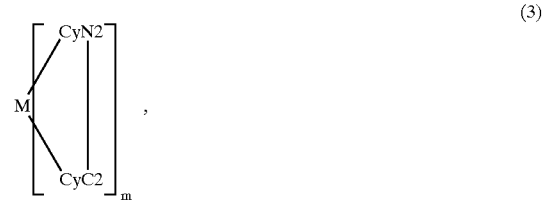

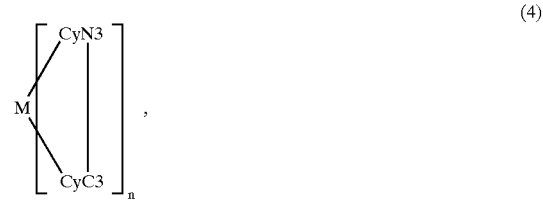

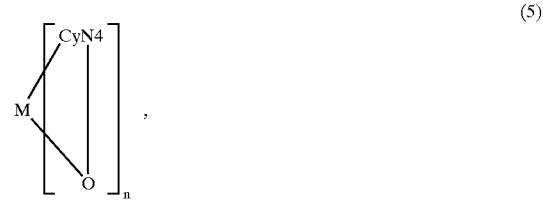

wherein CyN1, CyN2 and CyN3 independently denote a substituted or unsubstituted cyclic group containing a nitrogen atom connected to M; CyN4 denotes a cyclic group containing 8-quinoline or its derivative having a nitrogen atom connected to M; CyC1, CyC2 and CyC3 independently denote a substituted or unsubstituted cyclic group containing a carbon atom connected to M, with the proviso that the metal coordination compound is represented by the formula (2) when n is 0.

3 Claims, 5 Drawing Sheets

U.S. PATENT DOCUMENTS

| | | | | |
|---|---|---|---|---|
| 2002/0068190 | A1 * | 6/2002 | Tsuboyama et al. | 428/690 |
| 2002/0121638 | A1 * | 9/2002 | Grushin et al. | 257/40 |
| 2002/0190250 | A1 * | 12/2002 | Grushin et al. | 257/40 |

FOREIGN PATENT DOCUMENTS

| | | |
|---|---|---|
| EP | 1 191 613 A2 | 3/2002 |
| EP | 1 191 614 A2 | 3/2002 |
| EP | 1 238 981 A2 | 9/2002 |
| EP | 1 239 526 A2 | 9/2002 |
| EP | 1 244 155 A2 | 9/2002 |
| EP | 1 245 659 A1 | 10/2002 |
| JP | 8-319482 | 12/1996 |
| JP | 11-256148 | 9/1999 |
| JP | 11-329739 | 11/1999 |
| WO | WO 00/57676 A1 | 9/2000 |
| WO | WO 01/41512 A1 | 6/2001 |
| WO | WO 02/02714 A2 | 1/2002 |
| WO | WO 02/068435 A1 | 9/2002 |
| WO | WO 03/033617 A1 | 4/2003 |

OTHER PUBLICATIONS

D.F. O'Brien et al., "Improved Energy Transfer in Electrophosphorescent Devices," 74(3) *Applied Phys. Lett.* 442-444 (Jan. 1999).

M.A. Baldo et al. "Very High-Efficiency Green Organic Light-Emitting Devices Based on Electrophosphorescence," 75 (1) *Applied Phys. Lett.* 4-6 (Jul. 1999).

C.H. Chen et al., "Recent Developments in Molecular Organic Electroluminescent Materials," 125 *Macromol. Symp.* 1-48 (1997) no month.

Mark E. Thompson et al., "Electrophosphorescent Organic Light Emitting Diodes," *Conference Record of the 20th International Display Research Conference* 337-340 (2000) (no month).

Sergey Lamansky et al., "Highly Phosphorescent Bis-Cyclometallated Iridium Complexes: Synthesis, Photophysical Characterization, and Use in Organic Light Emitting Diodes," 123 *J. Am. Chem. Soc.* 4304-2312 (2001), published on Web Apr. 15, 2001.

K.A. King et al., "Excited-State Properties of a Triply Ortho-Metallated Iridium(III) Complex," 107(5) J. Am. Chem. Soc. 1431-1432 (1985) (Abstract Only) (no month).

Sergey Lamansky et al., "Molecularly Doped Polymer Light Emitting Diodes Utilizing Phosphorescent Pt(11) and Ir (111) Dopants," 2(1) *Organic Electronics* 53-62 (2001) (Abstract Only) (no month).

Vladimir V. Grushin et al., "New, Efficient Electroluminescent Materials Based on Organometallic Ir Complexes," 16 *Chemical Communications* 1494-1495 (2001) (Abstract Only) (no month).

* cited by examiner

METAL COORDINATION COMPOUND, LUMINESCENCE DEVICE AND DISPLAY APPARATUS

FIELD OF THE INVENTION AND RELATED ART

The present invention relates to a metal coordination compound, an organic luminescence device using the metal coordination compound and a display apparatus using the device. More specifically, the present invention relates to an organic metal coordination compound having a formula (1) appearing hereinafter as a luminescence material so as to allow stable luminescence efficiency, an organic luminescence device using the metal coordination compound and a display apparatus including the luminescence device.

An organic electroluminescence (EL) device has been extensively studied as a luminescence device with a high responsiveness and high efficiency.

The organic EL device generally has a sectional structure as shown in FIG. 1A or 1B (e.g., as described in "Macromol. Symp.", 125, pp. 1–48 (1997)).

Referring to the figures, the EL device generally has a structure including a transparent substrate 15, a transparent electrode 14 disposed on the transparent substrate 15, a metal electrode 11 disposed opposite to the transparent electrode 14, and a plurality of organic (compound) layers, as luminescence function layers, disposed between the transparent electrode 14 and the metal electrode 11.

Referring to FIG. 1A, the EL device in this embodiment has two organic layers including a luminescence layer 12 and a hole transport layer 13.

The transparent electrode 14 may be formed of a film of ITO (indium tin oxide) having a larger work function to ensure a good hole injection performance into the hole transport layer. On the other hand, the metal electrode 11 may be formed of a layer of aluminum, magnesium, alloys thereof, etc., having a smaller work function to ensure a good electron injection performance into the organic layer(s).

These (transparent and metal) electrodes 14 and 11 may be formed in a thickness of 50–200 nm.

The luminescence layer 12 may be formed of, e.g., aluminum quinolinol complex (representative example thereof may include Alq3 described hereinafter) having an electron transporting characteristic and a luminescent characteristic. The hole transport layer 13 may be formed of, e.g., biphenyldiamine derivative (representative example thereof may include α-NPD described hereinafter) having an electron donating characteristic.

The above-described EL device exhibits a rectification characteristic, so that when an electric field is applied between the metal electrode 11 as a cathode and the transparent electrode 14 as an anode, electrons are injected from the metal electrode 11 into the luminescence layer 12 and holes are injected from the transparent electrode 14.

The thus-injected holes and electrons are recombined within the luminescence layer 12 to produce excitons placed in an excited state, thus causing luminescence at the time of transition of the excitons to a ground state. At that time, the hole transport layer 13 functions as an electron-blocking layer to increase a recombination efficiency at the boundary between the luminescence layer 12 and the hole transport layer 13, thus enhancing a luminescence efficiency.

Referring to FIG. 1B, in addition to the layers shown in FIG. 1A, an electron transport layer 16 is disposed between the metal electrode 11 and the luminescence layer 12, whereby an effective carrier blocking performance can be ensured by separating functions of luminescence, electron transport and hole transport, thus allowing effective luminescence.

The electron transport layer 16 may be formed of, e.g., oxadiazole derivatives.

In ordinary organic EL devices, fluorescence caused during a transition of luminescent center molecule from a singlet excited state to a ground state is used as luminescence.

On the other hand, different from the above fluorescence (luminescence) via singlet exciton, phosphorescence (luminescence) via triplet exciton has been studied for use in organic EL device as described in, e.g., "Improved energy transfer in electrophosphorescent device" (D. F. O'Brien et al., Applied Physics Letters, Vol. 74, No. 3, pp. 442–444 (1999)) and "Very high-efficiency green organic light-emitting devices based on electrophosphorescence" (M. A. Baldo et al., Applied Physics Letters, Vol. 75, No. 1, pp. 4–6 (1999)).

The EL devices shown in these documents may generally have a sectional structure shown in FIG. 1C.

Referring to FIG. 1C, four organic layers including a hole transfer layer 13, a luminescence layer 12, an exciton diffusion-prevention layer 17, and an electron transport layer 16 are successively formed in this order on the transparent electrode (anode) 14.

In the above documents, higher efficiencies have been achieved by using four organic layers including a hole transport layer 13 of α-NPD (shown below), an electron transport layer 16 of Alq3 (shown below), an exciton diffusion-prevention layer 17 of BPC (shown below), and a luminescence layer 12 of a mixture of CPB (shown below) as a host material with Ir(ppy)₃ (shown below) or PtOEP (shown below) as a guest phosphorescence material doped into CBP at a concentration of ca. 6 wt. %.

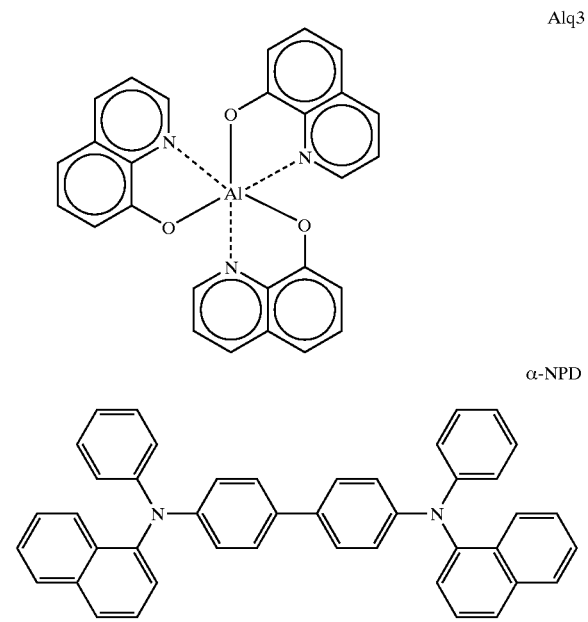

-continued

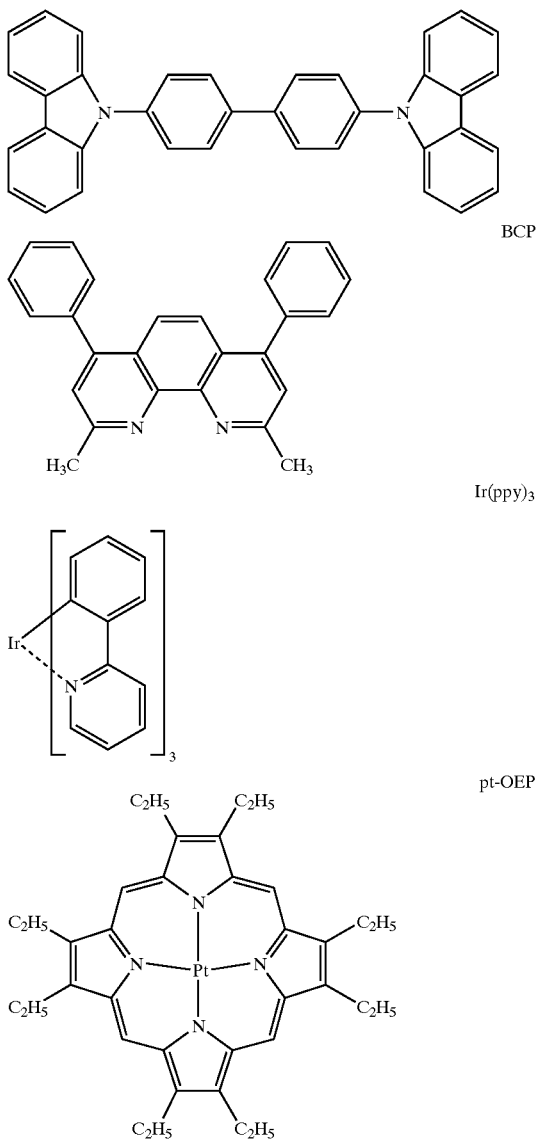

Alq3: tris(8-hydroxyquinoline) aluminum (aluminum-quinolinol complex),
α-NPD: N4,N4'-di-naphthalene-1-yl-N4,N4'-diphenyl-biphenyl-4,4'-diamine (4,4'-bis[N-(1-naphthyl)-N-phenyl-amino]biphenyl),
CBP: 4,4'-N,N'-dicarbazole-biphenyl,
BCP: 2,9-dimethyl-4,7-diphenyl-1,10-phenan-throline,
Ir(ppy)$_3$: fac tris(2-phenylpyridine)iridium (iridium-phenylpyridine complex), and
PtOEP: 2,3,7,8,12,13,17,18-octaethyl-21H,23H-porphine platinum (platinum-octaethyl porphine complex).

The phosphorescence (luminescence) material used in the luminescence layer 12 has particularly attracted notice. This is because the phosphorescence material is expected to provide a higher luminescence efficiency in principle.

More specifically, in the case of the phosphorescence material, excitons produced by recombination of carriers comprise singlet excitons and triplet excitons presented in a ratio of 1:3. For this reason, when fluorescence caused during the transition from the singlet excited state to the ground state is utilized, a resultant luminescence efficiency is 25% (as upper limit) based on all the produced excitons in principle.

On the other hand, in the case of utilizing phosphorescence caused during transition from the triplet excited state, a resultant luminescence efficiency is expected to be at least three times that of the case of fluorescence in principle. In addition thereto, if intersystem crossing from the singlet excited state (higher energy level) to the triplet excited state is taken into consideration, the luminescence efficiency of phosphorescence can be expected to be 100% (four times that of fluorescence) in principle.

The use of phosphorescence based on transition from the triplet excited state has also been proposed in, e.g., Japanese Laid-Open Patent Application (JP-A) 11-329739, JP-A 11-256148 and JP-A 8-319482.

However, the above-mentioned organic EL devices utilizing phosphorescence have accompanied with problems of a lower luminescence efficiency and stability thereof (luminescent deterioration) particularly in an energized state.

The reason for luminescent deterioration has not been clarified as yet but may be attributable to such a phenomenon that the life of triplet exciton is generally longer than that of singlet exciton by at least three digits, so that molecule is placed in a higher-energy state for a long period to cause reaction with ambient substance, formation of exciplex or excimer, change in minute molecular structure, structural change of ambient substance, etc.

Accordingly, a phosphorescence material for the (electro) phosphorescence EL device is required to provide a higher luminescence efficiency and a higher stability, to the EL device.

SUMMARY OF THE INVENTION

An object of the present invention is to provide a metal coordination compound as a material suitable for an organic layer of a luminescence device capable of providing a high-efficiency luminescent state at a high brightness (or luminance) for a long period while maintaining stability of the device.

Another object of the present invention is to provide a metal coordination compound allowing a higher phosphorescence yield and controlled emission (luminescence) wavelength as a phosphorescence (luminescence) material.

A further object to the present invention is to provide a metal coordination compound, as a multi-functional luminescence material, having not only a controlled luminescent characteristic but also controlled electrical characteristic, in view of a significance of the electrical characteristic of a luminescence material alone in the case where the luminescence material is employed in an organic EL device and is supplied with a current for luminescence.

A still further object of the present invention is to provide an organic luminescence device using the metal coordination compound and a display apparatus including the organic luminescence device.

According to the present invention, there is provided a metal coordination compound represented by the following formula (1):

$$L_mML'_n \qquad (1),$$

wherein M denotes Ir, Pt, Rh or Pd; L denotes a bidentate ligand; L' denotes a bidentate ligand different from L; m is an integer of 1, 2 or 3; and n is an integer of 0, 1 or 2 with the proviso that the sum of m and n is 2 or 3, the partial structure MLm being represented by a formula (2) or a formula (3) shown below, and the partial structure ML'n being represented by a formula (4) or a formula (5) shown below:

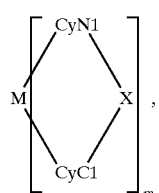
(2)

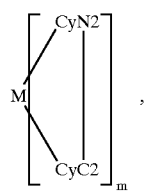
(3)

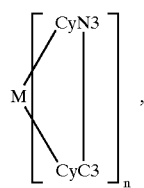
(4)

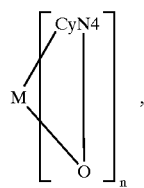
(5)

wherein CyN1, CyN2 and CyN3 independently denote a substituted or unsubstituted cyclic group containing a nitrogen atom connected to M; CyN4 denotes a cyclic group containing 8-quinoline or its derivative having a nitrogen atom connected to M; CyC1, CyC2 and CyC3 independently denote a substituted or unsubstituted cyclic group containing a carbon atom connected to M, each of substituents for CyN1, CyN2, CyN3, CyC1, CyC2 and CyC3 being selected from the group consisting of a halogen atom; cyano group; nitro group; a trialkylsilyl group containing three linear or branched alkyl groups each independently having 1–8 carbon atoms; a linear or branched alkyl group having 1–20 carbon atoms capable of including one or at least two non-neighboring methylene groups which can be replaced with —O—, —S—, —CO—, —CO—O—, —O—CO—, —CH=CH— or —C≡C— and capable of including a hydrogen atom which can be replaced with a fluorine atom; and an aromatic ring group capable of having a substituent selected from the group consisting of a halogen atom; cyano group; nitro group; and a linear or branched alkyl group having 1–20 carbon atoms capable of including one or at least two non-neighboring methylene groups which can be replaced with —O—, —S—, —CO—, —CO—O—, —O—CO—, —CH=CH— or —C≡C— and capable of including a hydrogen atom which can be replaced with a fluorine atom, CyN1 and CyC1 being connected via a covalent group containing X which is represented by —O—, —S—, —CO—, —C(R1)(R2)— or —NR— where R1, R2 and R independently denote a hydrogen atom, a halogen atom, an alkyl group, an alkyl group substituted with a halogen atom, a phenyl group or a naphthyl group, and CyN2 and CyC2, and CyN3 and CyC3 being independently connected via a covalent bond, with the proviso that the metal coordination compound is represented by the formula (2) when n is 0.

The metal coordination compound of the present invention exhibits phosphorescence at the time of energy transfer from an excited state to a ground state to provide a high luminescence efficiency.

According to the present invention, there is also provided an organic luminescence device, comprising: a substrate, a pair of electrodes disposed on the substrate, and a luminescence function layer disposed between the pair of electrodes comprising at least one species of an organic compound, wherein the organic compound comprises a metal coordination compound represented by the following formula (1):

$$LmML'n \qquad (1),$$

wherein M denotes Ir, Pt, Rh or Pd; L denotes a bidentate ligand; L' denotes a bidentate ligand different from L; m is an integer of 1, 2 or 3; and n is an integer of 0, 1 or 2 with the proviso that the sum of m and n is 2 or 3, the partial structure MLm being represented by a formula (2) or a formula (3) shown below, and the partial structure ML'n being represented by a formula (4) or a formula (5) shown below:

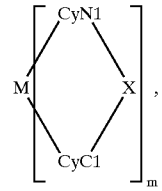
(2)

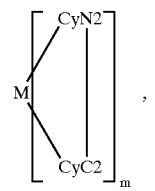
(3)

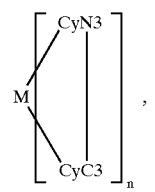
(4)

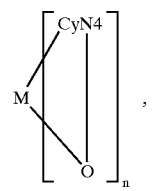
(5)

wherein CyN1, CyN2 and CyN3 independently denote a substituted or unsubstituted cyclic group containing a nitrogen atom connected to M; CyN4 denotes a cyclic group containing 8-quinoline or its derivative having a nitrogen atom connected to M; CyC1, CyC2 and CyC3 independently denote a substituted or unsubstituted cyclic group containing a carbon atom connected to M, each of substituents for CyN1, CyN2, CyN3, CyC1, CyC2 and CyC3 being selected from the group consisting of a halogen atom; cyano group; nitro group; a trialkylsilyl group containing three linear or branched alkyl groups each independently having 1–8 carbon atoms; a linear or branched alkyl group having 1–20 carbon atoms capable of including one or at least two non-neighboring methylene groups which can be replaced with —O—, —S—, —CO—, —CO—O—, —O—CO—, —CH=CH— or —C≡C— and capable of including a hydrogen atom which can be replaced with a fluorine atom; and an aromatic ring group capable of having a substituent selected from the group consisting of a halogen atom; cyano group; nitro group; and a linear or branched alkyl group having 1–20 carbon atoms capable of including one or at least two non-neighboring methylene groups which can be replaced with —O—, —S—, —CO—, —CO—O—, —O—CO—, —CH=CH— or —C≡C— and capable of including a hydrogen atom which can be replaced with a fluorine atom, CyN1 and CyC1 being connected via a covalent group containing X which is represented by —O—, —S—, —CO—, —C(R1)(R2)— or —NR— where R1, R2 and R independently denote a hydrogen atom, a halogen atom, an alkyl group, an alkyl group substituted with a halogen atom, a phenyl group or a naphthyl group, and CyN2 and CyC2, and CyN3 and CyC3 being independently connected via a covalent bond, with the proviso that the metal coordination compound is represented by the formula (2) when n is 0.

By applying a voltage between the pair of electrodes of the organic luminescence device to cause phosphorescence from the organic compound layer (luminescence function layer) containing the metal coordination compound.

According to the present invention, there is further provided an image display apparatus including the organic luminescence device and means for supplying electrical signals to the organic luminescence device.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1A:
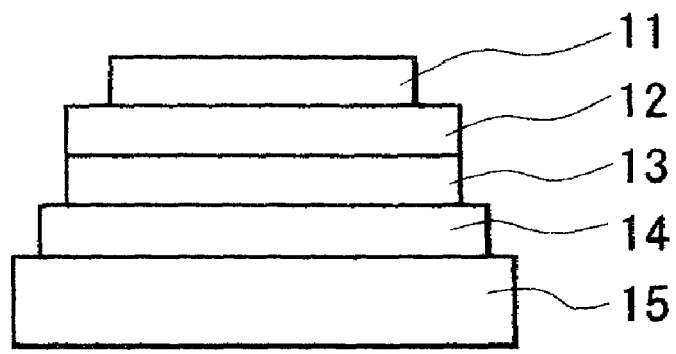
FIGS. 1A, 1B and 1C are respectively a schematic sectional view of a layer structure of an organic luminescence device.

In the case where a luminescence layer for an organic EL device is formed of a carrier transporting host material and a phosphorescent guest material, a process of emission of light (phosphorescence) may generally involve the following steps:

(1) transport of electron and hole within a luminescence layer,
(2) formation of exciton of the host material,
(3) transmission of excited energy between host material molecules,
(4) transmission of excited energy from the host material molecule to the guest material molecule,
(5) formation of triplet exciton of the guest material, and
(6) emission of light (phosphorescence) caused during transition from the triplet excited state to the ground state of the guest material.

In the above steps, desired energy transmission and luminescence may generally be caused based on various quenching and competition.

In order to improve a luminescence efficiency of the EL device, a luminescence center material per se is required to provide a higher yield of luminescence quantum. In addition thereto, an efficient energy transfer between host material molecules and/or between host material molecule and guest material molecule is also an important factor.

Further, the above-described luminescent deterioration in energized state may presumably relate to the luminescent center material per se or an environmental change thereof by its ambient molecular structure.

The metal coordination compound represented by the above formula (1) according to the present invention causes phosphorescence (luminescence) and is assumed to have a lowest excited state comprising a triplet excited state liable to cause metal-to-ligand charge transfer (MLCT* state) or $\pi$–$\pi$* state as a ligand-centered triplet excited state. The phosphorescent emission of light (phosphorescence) is caused to occur during the transition from the MLCT* state or $\pi$–$\pi$* state to the ground state.

The metal coordination compound of formula (1) according to the present invention has been found to provide a higher phosphorescence yield of at least 0.01 and a shorter phosphorescence life of 1–100 $\mu$sec.

The shorter phosphorescence life is necessary to provide a resultant EL device with a higher luminescence efficiency. This is because the longer phosphorescence life increases molecules placed in their triplet excited state which is a waiting state for phosphorescence, thus lowering the resultant luminescence efficiency particularly at a higher current density.

Accordingly, the metal coordination compound of formula (1) according to the present invention is a suitable luminescent material for an organic EL device with a higher phosphorescence yield and a shorter phosphorescence life.

Further, due to the shorter phosphorescence life, molecules of the metal coordination compound of formula (1) have a shorter time period wherein they stay in the triplet excited state, i.e. a higher energy state, thus providing the resultant EL device with improved durability and less deterioration in device characteristic. In this regard, the metal coordination compound according to the present invention has been substantiated to exhibit excellent stability of luminance as shown in Examples described hereinafter.

Figure 1B:
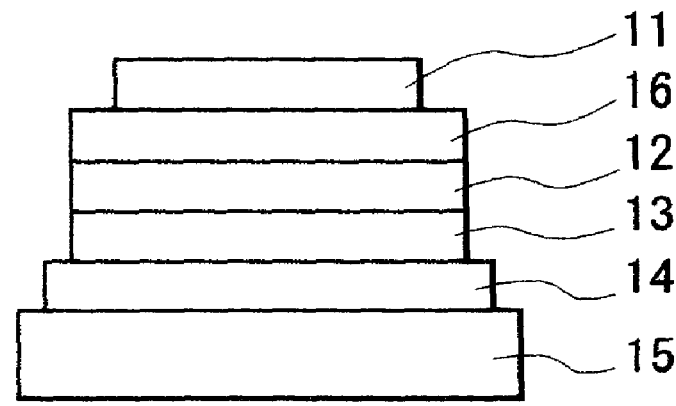
Figure 1C:
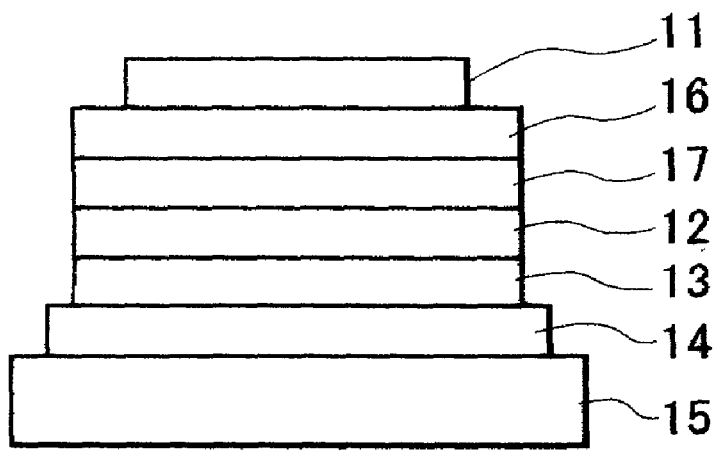

The organic luminescence device according to the present invention has a layer structure wherein an organic compound layer (luminescence function layer) comprising the metal coordination compound of the formula (1) is sandwiched between a pair of oppositely disposed electrodes as shown in FIGS. 1A to 1C. The organic luminescence device exhibits phosphorescence from the organic compound layer by applying a voltage between the pair of electrodes.

The metal coordination compound of the formula (1) according to the present invention used in the organic luminescence device (EL device) as a luminescence function material, particularly a luminescent material may be roughly classified into the following two compounds:
(1) a metal coordination compound having a molecular structure containing the same species of plural (two or three) ligands, and
(2) a metal coordination compound having a molecular structure containing different species of plural ligands.

In the present invention, it is possible to appropriately design a molecular structure of metal coordination compound so as to provide a stably high luminescence efficiency and maximum luminescence wavelength by using ligands different in structure in either case (of the above (1) and (2)).

In the case (1) using the same species of ligands, it is possible to provide a smaller half-width of luminescence spectrum and a higher color purity.

Further, in the case (2) using different species of ligands, it is possible to employ two different ligands for the metal coordination compound of the formula (1), thus imparting a plurality of functions (multi-function) to the metal coordination compound based on the respective features of the ligands. The impartition of multi-function is a characteristic feature of the use of different species of ligands. Particularly, in the case where the metal coordination compound having different species of ligands is used in an organic EL device, incorporation into the metal coordination compound of different species of ligands capable of imparting controlled luminescence and current characteristics to the EL device is very advantageous to the EL device since device characteristics of the EL device is largely affected by not only the luminescence characteristic but also the current characteristic.

An organic luminescence device using a phosphorescence material having different ligand structure has been described in M. E. Thompson et al., "Electrophotophorescent Organic Light Emitting Diodes" (Conference record of the 20th International Display Research Conference), pp. 337–340 (2000). In this document, Ir coordination compounds having luminescent ligands containing a phenylpyridine skeleton or a thienylpyridine skeleton and an additional ligand containing an acetylacetone skeleton. By using the Ir coordination compounds, a synthesis yield is improved without lowering a luminescence characteristic compared with Ir complex having (identical) three ligands of phenylpyridine (tris-acetylacetonato-Ir complex).

However, the tris-acetylacetonato-Ir complex exhibits no or a slight phosphorescence and has no carrier (hole/electron) transport performance.

In the above document, the acetylacetone ligand ((acac) ligand) is employed for the purpose of improving the synthesis yield without impairing the luminescence performance as described above, thus failing to positively suggesting improvement in device characteristics of an organic EL device.

According to our experiment, the device characteristics of the organic EL device have been found to be improved by imparting functions described below to different two ligands constituting a different ligand structure.

In order to determine an inherent feature of a ligand, at first, a metal coordination compound having one metal connected with the same species of ligands is synthesized and subjected to measurement of its characteristics (affected by a combination of the metal with the ligands), such as a (maximum) luminescence wavelength (emission wavelength), a luminescence yield, an electron transfer performance, a hole transfer performance and a thermal stability.

In this regard, in order to determine the luminescence characteristics including the luminescence wavelength and yield, a characteristic of luminescence molecules placed in a minimum excited state is an important factor.

As described above, the minimum excited state of the metal coordination compound of the formula (1) according to the present invention is the MLCT excited state or the ligand-centered excited state. In the case of a phosphorescence material, the MLCT excited state is generally advantageous thereto since the phosphorescence material (placed in the MLCT excited state) has a higher luminescence transition probability and a stronger luminescence performance in many cases.

Based on a combination of ligands and a (central) metal, a resultant metal coordination compound is determined whether its excited state is the MLCT excited state or the ligand-centered excited state.

Herein, the terms "MLCT (metal to ligand charge transfer) excited state" refers to an excited state formed by localization of electron orbit of molecules constituting the metal coordination compound towards the ligand side, thus causing a transfer of one electron side, thus causing a transfer of one electron from the metal to the ligand. On the other hand, the term "ligand-centered excited state" refers to an excited state formed within the ligands without being directly affected by the metal at the time of excitation. Generally, an electron is excited from bonding π-orbital to nonbonding π-orbital. Accordingly, the ligand-centered excited state is also called "π–π* excited state".

The carrier (hole/electron) transfer performance or ability may, e.g., be evaluated by measuring an increased amount of a current value flowing between a pair of electrodes sandwiching an organic compound layer (luminescence function layer) containing dispersed metal coordination compound having the same species of ligands, relative to that in the case of using no metal coordination compound.

Further, it is possible to determine whether H the organic compound layer is an electron transport layer or a hole transport layer by comparing a current characteristic of an organic luminescence device having a multi-layer structure including two organic compound layers sandwiching a luminescence layer therebetween with respect to various organic compounds constituting organic compound layers.

As described above, it becomes possible to characterize ligands constituting the metal coordination compound of the present invention by appropriately changing a combination of the metal and ligands.

Then, in order to improve the luminescence characteristics of a metal coordination compound having a different ligand structure, we presume that it is preferred to smoothly effect excited energy transition between ligands placed in their excited states to cause luminescence based on a particular ligand while minimizing the number of luminescent ligand.

More specifically, when a metal coordination compound having three ligands including one luminescent ligand is placed in excited state, excited energy is transferred from two ligands to one luminescent ligand, thus allowing a monochromatic luminescent color and an increased color purity. Further, it is expected that the use of one luminescent ligand decreases a probability of occurrence of energy transition between spatially adjacent molecules of the metal coordination compound, thus resulting in a decrease in quenching or deactivated energy.

Accordingly, in the present invention, a preferred class of combinations of a plurality of ligands may include:

(a) a combination of ligands including at least one ligand capable of being placed in the MLCT excited state,
(b) a combination of ligands including both of a luminescent ligand and a carrier transport ligand,
(c) a combination of ligands including a first ligand providing a longer maximum luminescence wavelength λ1 (i.e., smaller excited energy) and a second ligand providing a shorter maximum luminescence wavelength λ2 (<λ1) (i.e., larger excited energy) wherein the number of the first ligand is smaller than that of the second ligand, and
(d) a combination of ligands including a stronger luminescent ligand and a weaker luminescent ligand wherein the number of the stronger luminescent ligand is smaller than that of the weaker luminescent ligand.

The above ligand combinations (a) to (d) will be described below more specifically by taking Ir complexes as an example.

Formula 41

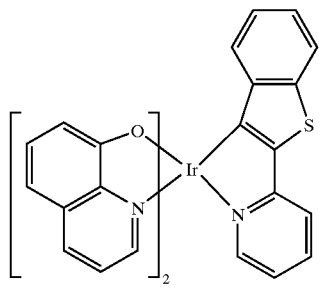

Formula 42

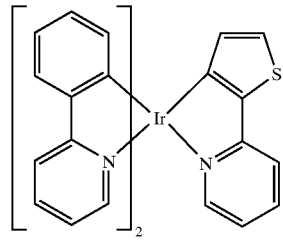

Formula 43

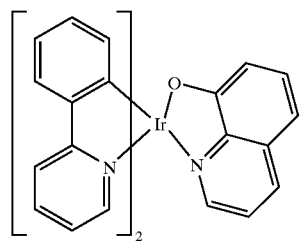

Formula 44

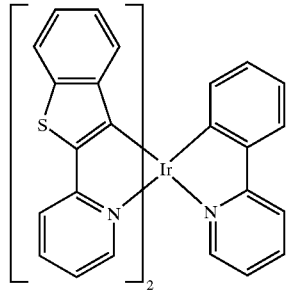

Formula 45

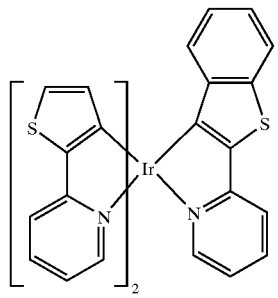

Formula 46

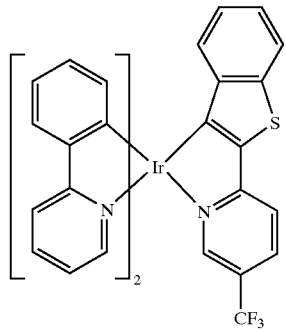

Formula 47

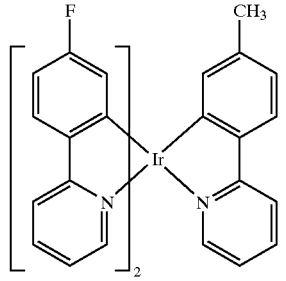

Formula 48

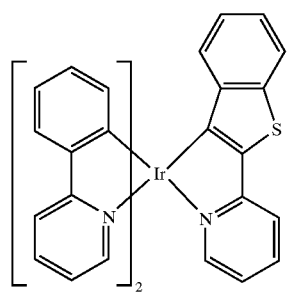

-continued

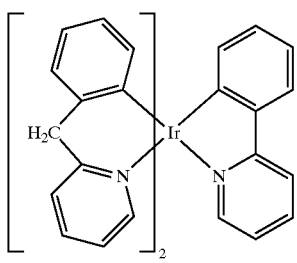

Formula 49

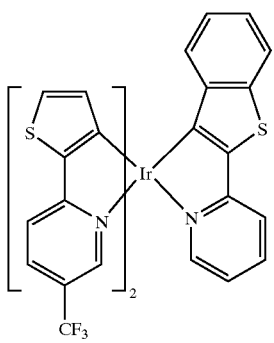

Formula 50

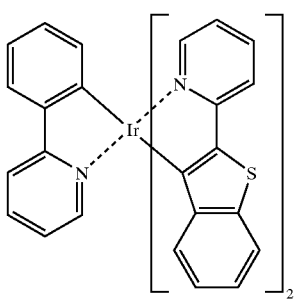

Formula 51

The metal coordination compounds having the above structural formulas 41 to 51 may be classified as follows.

| Combination | Formula |
|---|---|
| (a) | 41, 42, 43 |
| (b) | 44, 45 |
| (c) | 46, 47, 48, 49 |
| (d) | 48, 50 |

The metal coordination compounds of the formulas 41–51 includes those which can be embraced in a plurality of the combinations (a)–(d).

Combination (a)

The metal coordination compound of the formula 41 has two phenylpyridine ligands and one thienylpyridine ligand respectively connected to Ir (center metal). When the metal coordination compound is excited, the phenylpyridine ligands are placed in the MLCT excited state and the thienylpyridine ligand is placed in the ligand-centered excited state.

Figure 4A:
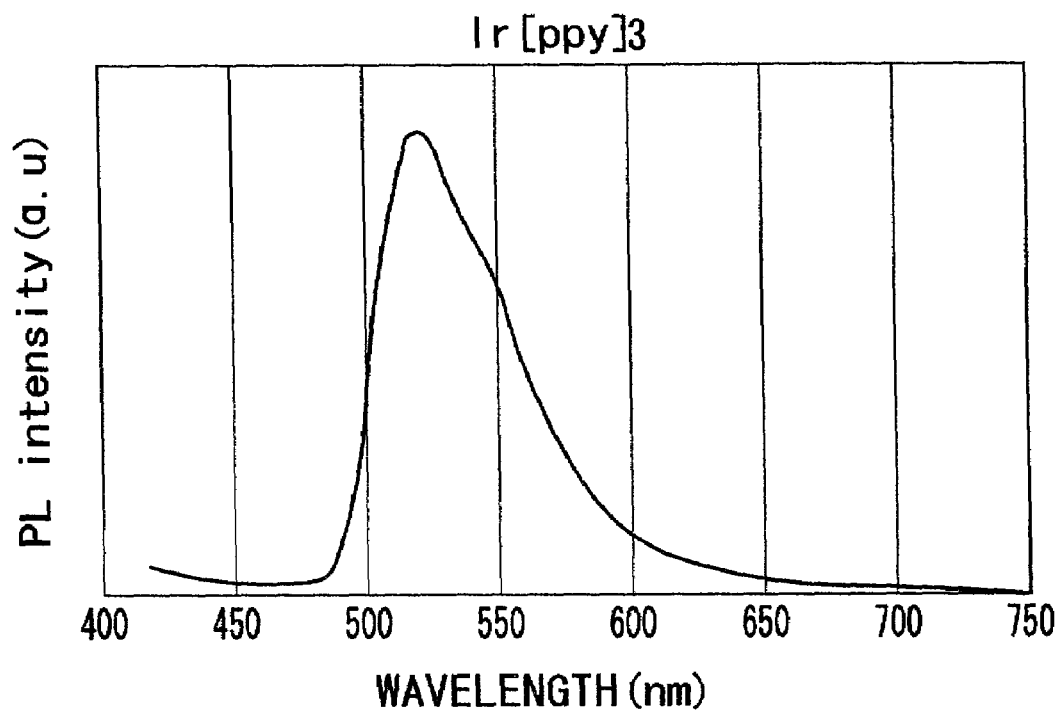
FIG. 4A shows luminescence spectrum diagram of a phenylpyridine-based Ir complex (Ir(ppy)$_3$)
Figure 4B:
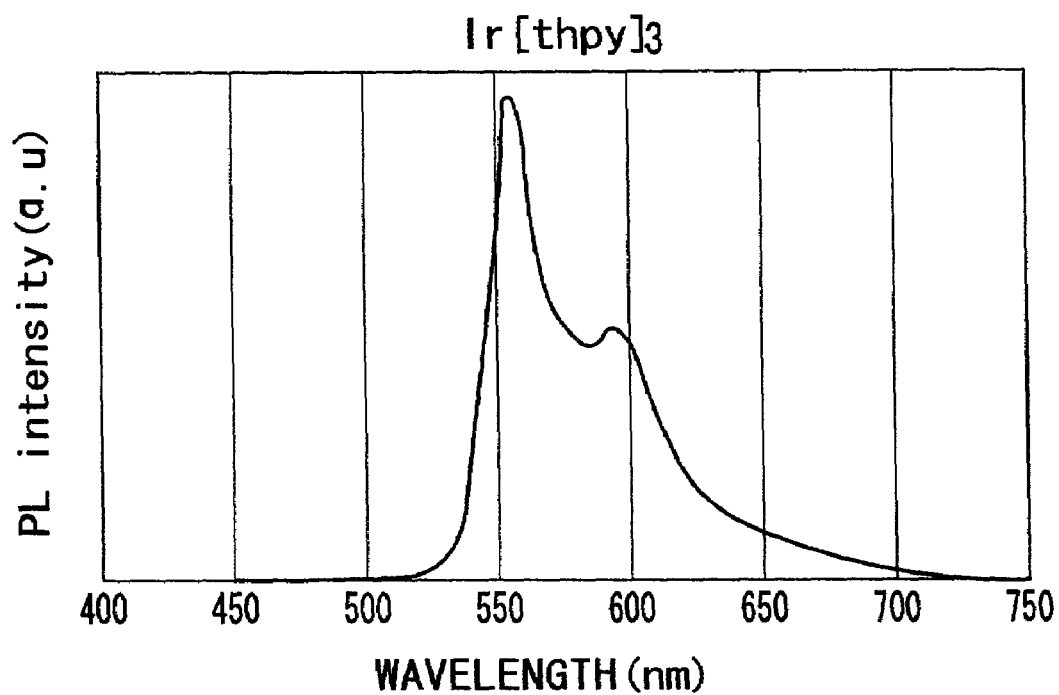
FIG. 4B shows a luminescence spectrum diagram of a thienylpyridine-based Ir complex (Ir(thpy)$_3$).

The excited state (MLCT or ligand-centered excited state) is identified based on shapes of emission spectra of Ir complex having three phenylpyridine skeletons (Ir(ppy)$_3$) and Ir complex having three thienylpyridine skeletons (Ir(thpy)$_3$), diagrams of which are shown in FIGS. 4A and 4B, respectively.

Referring to FIG. 4A, Ir(ppy)$_3$ shows no peak other than a main peak. On the other hand, as shown in FIG. 4B, Ir(thpy)$_3$ shows a sub-peak (or shoulder) other than a main peak on the longer wavelength side. This sub-peak is resulting from a vibrational level of an aromatic ligand and thus is not observed in the case of the MLCT excited state.

In the case of phosphorescence, compared with the case of the ligand-centered excited state, the case of the MLCT excited state is considerably allowed to exhibit transition with luminescence (phosphorescence) from the excited state to the ground state. Further, a probability of such transition is higher than that of transition with no radiation, thus generally providing a higher phosphorescence yield.

Ir(ppy)$_3$ shows no sub-peak as in the case of Ir(thpy)$_3$, thus being identified to be placed in the MLCT excited state.

Accordingly, in the case of the metal coordination compound of the formula 41, when the phenylpyridine ligand is first excited, the excitation energy is not quenched or deactivated but is quickly intramolecular-transferred to the thienylpyridine ligand to place the thienylpyridine ligand in an excited state. This is because the triplet energy level of phenylpyridine is higher than that of thienylpyridine.

Even in both the case of an organic EL device and the case of photoluminescence (PL) in a photo-excitation solution, luminescence at 550 nm resulting from the thienylpyridine ligand is observed.

Similarly, the 8-quinolinol ligand in the metal coordination compound of the formula 42 and the benzothienylpyridine ligand in the metal coordination compound of the formula 43 are ligands placed in the ligand-centered excited state. In these cases of using the metal coordination compounds of the formula 42 and 43, luminescences resulting from the 8-quinolinol ligand and the benzothienylpyridine ligand as a longer-wavelength luminescent ligand are observed, respectively.

In the case where a ligand in the MLCT excited state provides a longer maximum luminescence wavelength, luminescence resulting from the ligand in the MLCT excited state.

Further, for example, in the case of the metal coordination compound of the formula 48 having the 4-fluorophenylpyridine ligand and the 4-methylphenylpyridine ligand both in the MLCT excited state, quenching with no luminescence is not readily caused to occur.

The maximum luminescence wavelength of the 4-fluorophenylpyridine is shorter than (i.e., excitation energy level thereof is higher than) that of the 4-methylphenylpyridine. Accordingly, even when either ligand is excited, excitation energy is intramolecular-transferred to the 4-methylphenylpyridine ligand with a lower excitation energy level to cause luminescence resulting from the 4-methylphenylpyridine. The metal coordination compound of the formula 48 is thus placed in the MLCT excited state, thus not readily causing quenching with no radiation to allow a high-efficiency luminescence.

Accordingly, when the metal coordination compound of the present invention has a different ligand structure including a ligand capable of being placed in the MLCT excited state, it becomes possible to effect intramolecular energy transition at a high efficiency, thus ensuring a high phosphorescence yield.

Combination (b)

The metal coordination compound of the formula 44 has the f-quinolinol ligand as an electron transport ligand and the benzothienylpyridine ligand as a luminescent ligand. When the metal coordination compound of the formula 44 is dispersed in the luminescence layer 12 of the organic EL device shown in FIG. 1C, it is possible to improve a luminescence efficiency compared with the case of using a metal coordination compound having the same ligand structure comprising three f-quinolinol ligands (i.e., tris-8-quinolinolato-Ir complex).

Further, when compared with an organic EL device using no luminescence material (the metal coordination compound of the formula 44 in this case), the organic EL device using the metal coordination compound of the formula 44 effectively improves a resultant current density under application of an identical voltage. This may be attributable to such a mechanism that the electron transport 8-quinolinol ligand allows supply of electrons to the luminescence layer (into which carrier electrons are ordinarily to readily injected) by dispersing the metal coordination compound of the formula 44 in the luminescence layer, thus forming excitons by combination with holes to ensure efficient luminescence based on the luminescence benzothienylpyridine ligand.

The benzothienylpyridine ligand also exhibits a hole transport performance. In the metal coordination compound of the formula 45, the benzothienylpyridine ligand has a hole transport function.

Combination (c)

The metal coordination compound of the formula 46 has the thienylpyridine ligand and the benzothienylpyridine ligand.

An Ir complex having three thienylpyridine ligands and an Ir complex having three benzothienyl-pyridine ligands causes phosphorescence at maximum luminescence wavelengths of 550 nm and 600 nm, respectively. Accordingly, the latter Ir complex has a longer maximum luminescence wavelength and a smaller lowest excitation energy (triplet energy in this case). Luminescence resulting from the benzothienyl-pyridine ligand is observed both in the case of an organic EL device using the metal coordination compound of the formula 46 and in the case of PL (photoluminescence) in a photo-excitation solution thereof.

When an organic EL device shown in FIG. 1C is prepared by using the metal coordination compound of the formula 46, it is possible to obtain a high luminescence efficiency. This may be attributable to such a mechanism that, compared with a metal coordination compound having (identical) three benzothienylpyridine ligands (luminescent ligands), the number of luminescent ligand in the metal coordination compound of the formula 46 is ⅓ of the metal coordination compound having three benzothienyl-pyridine ligands to decrease a probability of formation of quenching path with no luminescence by intermolecular interaction with ambient molecules.

Accordingly, it becomes possible to realize a high luminescence efficiency by decreasing the number of the longer-wavelength luminescent ligand relative to that of the shorter-wavelength luminescent ligand.

With respect to the metal coordination compound of the formula 49, the benzylpyridine ligand exhibits a blue luminescence characteristic (emission peak wavelength: 480 nm) and the phenylpyridine ligand exhibits a green luminescence characteristic (emission peak wavelength: 515 nm).

As a result, excitation energy is concentrated on the phenylpyridine ligand, thus ensuring stable luminescence resulting from the phenylpyridine ligand.

Combination (d)

The metal coordination compound of the formula 50 has the thienyl-4-trifluoromethylpyridine ligand and the benzothienylpyridine ligand.

According to our experiment as to luminescence characteristic in a solution (e.g., in deoxidized toluene), a photo-excitation phosphorescence yield in the solution of an Ir complex having three thienyl-4-trifluoromethylpyridine ligands is smaller than that of an Ir complex having three benzothienylpyridine ligands. Accordingly, the benzothienylpyridine ligand is a relatively stronger luminescent ligand compared with the thienyl-4-trifluoromethylpyridine ligand. Further, the former ligand also provides a relatively longer maximum luminescence wavelength (i.e., a relatively lower excitation energy level). For this reason, luminescence from the metal coordination compound of the formula 49 is one resulting from the benzo-thienylpyridine ligands based on intramolecular energy transfer.

By using the metal coordination compound of the formula 49 in a luminescence layer 12 for an organic EL device shown in FIG. 1C, a high luminescence efficiency is achieved.

Accordingly, it is possible to improve a luminescence efficiency by decreasing the number (1 in this case) of stronger luminescent ligand and longer-wavelength luminescent ligand.

As described above, the metal coordination compound of the present invention satisfying at least one of the above-mentioned combinations (a) to (d) effectively functions as a luminescence function material and provides a resultant organic EL device with a high luminescence efficiency. In the present invention, it is generally expected to increase the luminescence efficiency by ca. 20% when compared with the case of using a metal coordination compound having identical three luminescent ligands, but a degree of increase in luminescence efficiency may vary depending on species of the metal and ligands.

The above-mentioned high-efficiency organic luminescence device may be applicable to various products requiring energy saving and high luminescence, such as light sources for a display apparatus, illumination apparatus, printers, etc., and a backlight for a liquid crystal display apparatus.

When the organic luminescence device of the present invention is used as an image display apparatus, it becomes possible to provide flat-panel displays with advantages such as a good energy saving performance, high visibility, and lightweight properties.

The organic luminescence device of the present invention is also prepared in a single matrix-type display device using intersecting stripe electrodes at right angles or an active matrix-type display device including a matrix of pixels each provided with, e.g., at least one TFT (thin film transistor), such as amorphous TFT or polycrystalline TFT.

When the organic luminescence device of the present invention is used as a light source for a printer, e.g., as a laser light source for a laser beam printer, independently addressable elements are arranged in an array and a photosensitive drum is subjected to desired exposure, thus effecting image formation. By the use of the organic luminescence device of the present invention, it becomes possible to considerably reduce the apparatus size (volume).

With respect to the illumination apparatus and the backlight, it is expected that the organic luminescence device of the present invention effectively exhibits an excellent energy saving effect.

Hereinbelow, specific examples of the metal coordination compound of the formula (1) according to the present invention will be shown in Table 1. The metal coordination compound of the present invention is however not restricted to these specific examples.

In Table 1, abbreviations Ph to Pz for CyN1, CyN2, CyN3, CyC1, CyC2 and CyC3 and those O to CR2 for —X— represent the following divalent groups, respectively.

Ph:

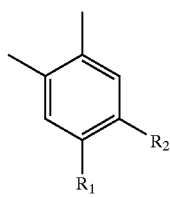

Tn1:

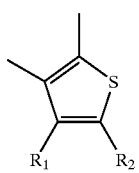

Tn2:

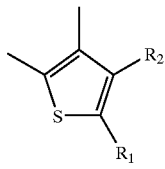

Tn3:

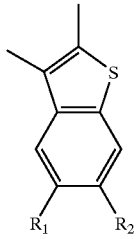

Np:

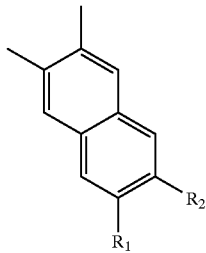

-continued

Qn1:

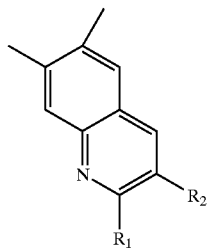

Qn2:

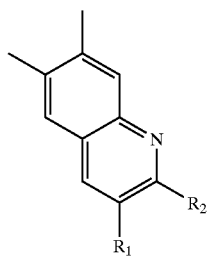

Qx:

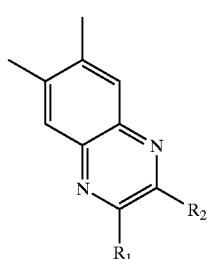

Qz1:

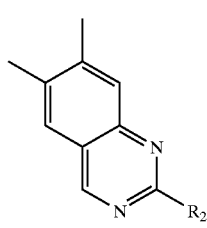

Qz2:

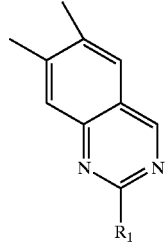

Cn1:

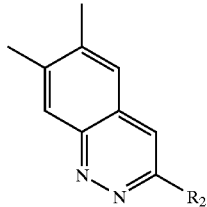

Cn2:
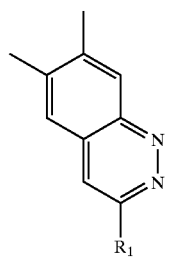
Pz:
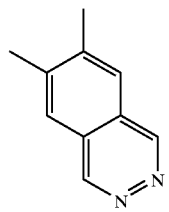
Pr:
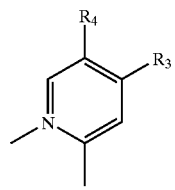
Pd:
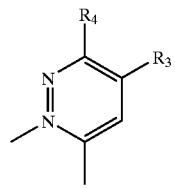
Py1:
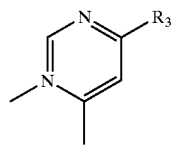
Pa:
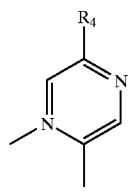
Py2:
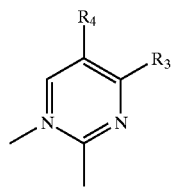
Pz:
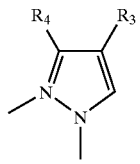
O:
S:
NR:
CO:
CR$_2$:
Further, formulas (11) to (14) corresponding to the partial structure ML'n as the formula (5) (including CyN4 being 8-quinolinol skeleton or its derivative) shown as L' in Table 1 for convenience represent the following structures, respectively.
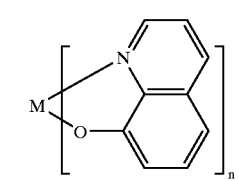
(11)
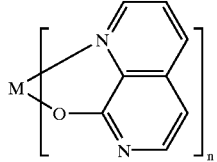
(12)
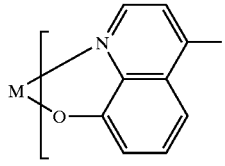
(13)

-continued

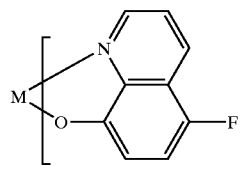
(14)

Further, Example Compounds Nos. 215 to 218 and 746 include an acetylacetone ligand as L' for another ligand of the formula (6).

TABLE 1

| No | M | m | n | CyN1 | \X/ | CyC1 | R1 | R2 | R3 | R4 | R5 | R6 | L' |
|---|---|---|---|---|---|---|---|---|---|---|---|---|---|
| 1 | Ir | 3 | 0 | Pr | O | Ph | H | H | H | H | | | |
| 2 | Ir | 3 | 0 | Pr | O | Tn1 | H | H | H | H | | | |
| 3 | Ir | 3 | 0 | Pr | O | Tn2 | H | H | H | H | | | |
| 4 | Ir | 3 | 0 | Pr | O | Tn3 | H | H | H | H | | | |
| 5 | Ir | 3 | 0 | Pr | O | Qn1 | H | H | H | H | | | |
| 6 | Ir | 3 | 0 | Pr | O | Qn2 | H | H | H | H | | | |
| 7 | Ir | 3 | 0 | Pr | O | Qx | H | H | H | H | | | |
| 8 | Ir | 3 | 0 | Pr | O | Qz1 | — | H | H | H | | | |
| 9 | Ir | 3 | 0 | Pr | O | Qz2 | H | — | H | H | | | |
| 10 | Ir | 3 | 0 | Pr | O | Cn1 | — | H | H | H | | | |
| 11 | Ir | 3 | 0 | Pr | O | Cn2 | H | — | H | H | | | |
| 12 | Ir | 3 | 0 | Pr | O | Pz | — | — | H | H | | | |
| 13 | Ir | 3 | 0 | Pr | S | Ph | H | H | H | H | | | |
| 14 | Ir | 3 | 0 | Pr | S | Tn1 | H | H | H | H | | | |
| 15 | Ir | 3 | 0 | Pr | S | Tn2 | H | H | H | H | | | |
| 16 | Ir | 3 | 0 | Pr | S | Tn3 | H | H | H | H | | | |
| 17 | Ir | 3 | 0 | Pr | S | Qn1 | H | H | H | H | | | |
| 18 | Ir | 3 | 0 | Pr | S | Qn2 | H | H | H | H | | | |
| 19 | Ir | 3 | 0 | Pr | S | Qx | H | H | H | H | | | |
| 20 | Ir | 3 | 0 | Pr | S | Qz1 | — | H | H | H | | | |
| 21 | Ir | 3 | 0 | Pr | S | Qz2 | H | — | H | H | | | |
| 22 | Ir | 3 | 0 | Pr | S | Cn1 | — | H | H | H | | | |
| 23 | Ir | 3 | 0 | Pr | S | Cn2 | H | — | H | H | | | |
| 24 | Ir | 3 | 0 | Pr | S | Pz | — | — | H | H | | | |
| 25 | Ir | 3 | 0 | Pr | NR | Ph | H | H | H | H | H | | |
| 26 | Ir | 3 | 0 | Pr | NR | Tn1 | H | H | H | H | H | | |
| 27 | Ir | 3 | 0 | Pr | NR | Tn2 | H | H | H | H | H | | |
| 28 | Ir | 3 | 0 | Pr | NR | Tn3 | H | H | H | H | H | | |
| 29 | Ir | 3 | 0 | Pr | NR | Qn1 | H | H | H | H | H | | |
| 30 | Ir | 3 | 0 | Pr | NR | Qn2 | H | H | H | H | H | | |
| 31 | Ir | 3 | 0 | Pr | NR | Qx | H | H | H | H | H | | |
| 32 | Ir | 3 | 0 | Pr | NR | Qz1 | — | H | H | H | H | | |
| 33 | Ir | 3 | 0 | Pr | NR | Qz2 | H | — | H | H | H | | |
| 34 | Ir | 3 | 0 | Pr | NR | Cn1 | — | H | H | H | H | | |
| 35 | Ir | 3 | 0 | Pr | NR | Cn2 | H | — | H | H | H | | |
| 36 | Ir | 3 | 0 | Pr | NR | Pz | — | — | H | H | H | | |
| 37 | Ir | 3 | 0 | Pr | CO | Ph | H | H | H | H | | | |
| 38 | Ir | 3 | 0 | Pr | CO | Tn1 | H | H | H | H | | | |
| 39 | Ir | 3 | 0 | Pr | CO | Tn2 | H | H | H | H | | | |
| 40 | Ir | 3 | 0 | Pr | CO | Tn3 | H | H | H | H | | | |
| 41 | Ir | 3 | 0 | Pr | CO | Qn1 | H | H | H | H | | | |
| 42 | Ir | 3 | 0 | Pr | CO | Qn2 | H | H | H | H | | | |
| 43 | Ir | 3 | 0 | Pr | CO | Qx | H | H | H | H | | | |
| 44 | Ir | 3 | 0 | Pr | CO | Qz1 | — | H | H | H | | | |
| 45 | Ir | 3 | 0 | Pr | CO | Qz2 | H | — | H | H | | | |
| 46 | Ir | 3 | 0 | Pr | CO | Cn1 | — | H | H | H | | | |
| 47 | Ir | 3 | 0 | Pr | CO | Cn2 | H | — | H | H | | | |
| 48 | Ir | 3 | 0 | Pr | CO | Pz | — | — | H | H | | | |
| 49 | Ir | 3 | 0 | Pr | CR2 | Ph | H | H | H | H | H | H | |
| 50 | Ir | 3 | 0 | Pr | CR2 | Tn1 | H | H | H | H | H | H | |
| 51 | Ir | 3 | 0 | Pr | CR2 | Tn2 | H | H | H | H | H | H | |
| 52 | Ir | 3 | 0 | Pr | CR2 | Tn3 | H | H | H | H | H | H | |
| 53 | Ir | 3 | 0 | Pr | CR2 | Qn1 | H | H | H | H | H | H | |
| 54 | Ir | 3 | 0 | Pr | CR2 | Qn2 | H | H | H | H | H | H | |
| 55 | Ir | 3 | 0 | Pr | CR2 | Qx | H | H | H | H | H | H | |
| 56 | Ir | 3 | 0 | Pr | CR2 | Qz1 | — | H | H | H | H | H | |
| 57 | Ir | 3 | 0 | Pr | CR2 | Qx2 | H | — | H | H | H | H | |

TABLE 1-continued

| # | M | a | b | L1 | L2 | L3 | c1 | c2 | c3 | c4 | c5 | c6 |
|---|---|---|---|----|----|----|----|----|----|----|----|----|
| 58 | Ir | 3 | 0 | Pr | CR2 | Cn1 | — | H | H | H | H | H |
| 59 | Ir | 3 | 0 | Pr | CR2 | Cn2 | H | — | H | H | H | H |
| 60 | Ir | 3 | 0 | Pr | CR2 | Pz | — | — | H | H | H | H |
| 61 | Ir | 3 | 0 | Pd | O | Ph | H | H | H | H | | |
| 62 | Ir | 3 | 0 | Pd | O | Tn1 | H | H | H | H | | |
| 63 | Ir | 3 | 0 | Pd | O | Tn2 | H | H | H | H | | |
| 64 | Ir | 3 | 0 | Pd | O | Tn3 | H | H | H | H | | |
| 65 | Ir | 3 | 0 | Pd | S | Ph | H | H | H | H | | |
| 66 | Ir | 3 | 0 | Pd | S | Tn1 | H | H | H | H | | |
| 67 | Ir | 3 | 0 | Pd | S | Tn2 | H | H | H | H | | |
| 68 | Ir | 3 | 0 | Pd | S | Tn3 | H | H | H | H | | |
| 69 | Ir | 3 | 0 | Pd | NR | Ph | H | H | H | H | H | |
| 70 | Ir | 3 | 0 | Pd | NR | Tn1 | H | H | H | H | H | |
| 71 | Ir | 3 | 0 | Pd | NR | Tn2 | H | H | H | H | H | |
| 72 | Ir | 3 | 0 | Pd | NR | Tn3 | H | H | H | H | H | |
| 73 | Ir | 3 | 0 | Pd | CO | Ph | H | H | H | H | | |
| 74 | Ir | 3 | 0 | Pd | CO | Tn1 | H | H | H | H | | |
| 75 | Ir | 3 | 0 | Pd | CO | Tn2 | H | H | H | H | | |
| 76 | Ir | 3 | 0 | Pd | CO | Tn3 | H | H | H | H | | |
| 77 | Ir | 3 | 0 | Pd | CR2 | Ph | H | H | H | H | H | H |
| 78 | Ir | 3 | 0 | Pd | CR2 | Tn1 | H | H | H | H | H | H |
| 79 | Ir | 3 | 0 | Pd | CR2 | Tn2 | H | H | H | H | H | H |
| 80 | Ir | 3 | 0 | Pd | CR2 | Tn3 | H | H | H | H | H | H |
| 81 | Ir | 3 | 0 | Pr1 | O | Ph | H | H | H | — | | |
| 82 | Ir | 3 | 0 | Pr1 | O | Tn1 | H | H | H | — | | |
| 83 | Ir | 3 | 0 | Pr1 | O | Tn2 | H | H | H | — | | |
| 84 | Ir | 3 | 0 | Pr1 | O | Tn3 | H | H | H | — | | |
| 85 | Ir | 3 | 0 | Pr1 | S | Ph | H | H | H | — | | |
| 86 | Ir | 3 | 0 | Pr1 | S | Tn1 | H | H | H | — | | |
| 87 | Ir | 3 | 0 | Pr1 | S | Tn2 | H | H | H | — | | |
| 88 | Ir | 3 | 0 | Pr1 | S | Tn3 | H | H | H | — | | |
| 89 | Ir | 3 | 0 | Pr1 | NR | Ph | H | H | H | — | H | |
| 90 | Ir | 3 | 0 | Pr1 | NR | Tn1 | H | H | H | — | H | |
| 91 | Ir | 3 | 0 | Pr1 | NR | Tn2 | H | H | H | — | H | |
| 92 | Ir | 3 | 0 | Pr1 | NR | Tn3 | H | H | H | — | H | |
| 93 | Ir | 3 | 0 | Pr1 | CO | Ph | H | H | H | — | | |
| 94 | Ir | 3 | 0 | Pr1 | CO | Tn1 | H | H | H | — | | |
| 95 | Ir | 3 | 0 | Pr1 | CO | Tn2 | H | H | H | — | | |
| 96 | Ir | 3 | 0 | Pr1 | CO | Tn3 | H | H | H | — | | |
| 97 | Ir | 3 | 0 | Pr1 | CR2 | Ph | H | H | H | — | H | H |
| 98 | Ir | 3 | 0 | Pr1 | CR2 | Tn1 | H | H | H | — | H | H |
| 99 | Ir | 3 | 0 | Pr1 | CR2 | Tn2 | H | H | H | — | H | H |
| 100 | Ir | 3 | 0 | Pr1 | CR2 | Tn3 | H | H | H | — | H | H |
| 101 | Ir | 3 | 0 | Pa | O | Ph | H | H | — | H | | |
| 102 | Ir | 3 | 0 | Pa | O | Tn1 | H | H | — | H | | |
| 103 | Ir | 3 | 0 | Pa | O | Tn2 | H | H | — | H | | |
| 104 | Ir | 3 | 0 | Pa | O | Tn3 | H | H | — | H | | |
| 105 | Ir | 3 | 0 | Pa | S | Ph | H | H | — | H | | |
| 106 | Ir | 3 | 0 | Pa | S | Tn1 | H | H | — | H | | |
| 107 | Ir | 3 | 0 | Pa | S | Tn2 | H | H | — | H | | |
| 108 | Ir | 3 | 0 | Pa | S | Tn3 | H | H | — | H | | |
| 109 | Ir | 3 | 0 | Pa | NR | Ph | H | H | — | H | H | |
| 110 | Ir | 3 | 0 | Pa | NR | Tn1 | H | H | — | H | H | |
| 111 | Ir | 3 | 0 | Pa | NR | Tn2 | H | H | — | H | H | |
| 112 | Ir | 3 | 0 | Pa | NR | Tn3 | H | H | — | H | H | |
| 113 | Ir | 3 | 0 | Pa | CO | Ph | H | H | — | H | | |
| 114 | Ir | 3 | 0 | Pa | CO | Tn1 | H | H | — | H | | |
| 115 | Ir | 3 | 0 | Pa | CO | Tn2 | H | H | — | H | | |
| 116 | Ir | 3 | 0 | Pa | CO | Tn3 | H | H | — | H | | |
| 117 | Ir | 3 | 0 | Pa | CR2 | Ph | H | H | — | H | H | H |
| 118 | Ir | 3 | 0 | Pa | CR2 | Tn1 | H | H | — | H | H | H |
| 119 | Ir | 3 | 0 | Pa | CR2 | Tn2 | H | H | — | H | H | H |
| 120 | Ir | 3 | 0 | Pa | CR2 | Tn3 | H | H | — | H | H | H |
| 121 | Ir | 3 | 0 | Pr2 | O | Ph | H | H | H | H | | |
| 122 | Ir | 3 | 0 | Pr2 | O | Tn1 | H | H | H | H | | |
| 123 | Ir | 3 | 0 | Pr2 | O | Tn2 | H | H | H | H | | |
| 124 | Ir | 3 | 0 | Pr2 | O | Tn3 | H | H | H | H | | |
| 125 | Ir | 3 | 0 | Pr2 | S | Ph | H | H | H | H | | |
| 126 | Ir | 3 | 0 | Pr2 | S | Tn1 | H | H | H | H | | |
| 127 | Ir | 3 | 0 | Pr2 | S | Tn2 | H | H | H | H | | |
| 128 | Ir | 3 | 0 | Pr2 | S | Tn3 | H | H | H | H | | |
| 129 | Ir | 3 | 0 | Pr2 | NR | Ph | H | H | H | H | H | |
| 130 | Ir | 3 | 0 | Pr2 | NR | Tn1 | H | H | H | H | H | |
| 131 | Ir | 3 | 0 | Pr2 | NR | Tn2 | H | H | H | H | H | |
| 132 | Ir | 3 | 0 | Pr2 | NR | Tn3 | H | H | H | H | H | |
| 133 | Ir | 3 | 0 | Pr2 | CO | Ph | H | H | H | H | | |
| 134 | Ir | 3 | 0 | Pr2 | CO | Tn1 | H | H | H | H | | |
| 135 | Ir | 3 | 0 | Pr2 | CO | Tn2 | H | H | H | H | | |
| 136 | Ir | 3 | 0 | Pr2 | CO | Tn3 | H | H | H | H | | |

TABLE 1-continued

| | | | | | | | | | | | | |
|---|---|---|---|---|---|---|---|---|---|---|---|---|
| 137 | Ir | 3 | 0 | Pr2 | CR2 | Ph | H | H | H | H | H | |
| 138 | Ir | 3 | 0 | Pr2 | CR2 | Tn1 | H | H | H | H | H | |
| 139 | Ir | 3 | 0 | Pr2 | CR2 | Tn2 | H | H | H | H | H | |
| 140 | Ir | 3 | 0 | Pr2 | CR2 | Tn3 | H | H | H | H | H | |
| 141 | Ir | 3 | 0 | Pz | O | Ph | H | H | H | H | | |
| 142 | Ir | 3 | 0 | Pz | O | Tn1 | H | H | H | H | | |
| 143 | Ir | 3 | 0 | Pz | O | Tn2 | H | H | H | H | | |
| 144 | Ir | 3 | 0 | Pz | O | Tn3 | H | H | H | H | | |
| 145 | Ir | 3 | 0 | Pz | S | Ph | H | H | H | H | | |
| 146 | Ir | 3 | 0 | Pz | S | Tn1 | H | H | H | H | | |
| 147 | Ir | 3 | 0 | Pz | S | Tn2 | H | H | H | H | | |
| 148 | Ir | 3 | 0 | Pz | S | Tn3 | H | H | H | H | | |
| 149 | Ir | 3 | 0 | Pz | NR | Ph | H | H | H | H | H | |
| 150 | Ir | 3 | 0 | Pz | NR | Tn1 | H | H | H | H | H | |
| 151 | Ir | 3 | 0 | Pz | NR | Tn2 | H | H | H | H | H | |
| 152 | Ir | 3 | 0 | Pz | NR | Tn3 | H | H | H | H | H | |
| 153 | Ir | 3 | 0 | Pz | CO | Ph | H | H | H | H | | |
| 154 | Ir | 3 | 0 | Pz | CO | Tn1 | H | H | H | H | | |
| 155 | Ir | 3 | 0 | Pz | CO | Tn2 | H | H | H | H | | |
| 156 | Ir | 3 | 0 | Pz | CO | Tn3 | H | H | H | H | | |
| 157 | Ir | 3 | 0 | Pz | CR2 | Ph | H | H | H | H | H | H |
| 158 | Ir | 3 | 0 | Pz | CR2 | Tn1 | H | H | H | H | H | H |
| 159 | Ir | 3 | 0 | Pz | CR2 | Tn2 | H | H | H | H | H | H |
| 160 | Ir | 3 | 0 | Pz | CR2 | Tn3 | H | H | H | H | H | H |
| 161 | Ir | 3 | 0 | Pr | NR | Ph | H | H | H | H | phenyl | |
| 162 | Ir | 3 | 0 | Pr | NR | Ph | H | H | H | H | naphthyl | |
| 163 | Ir | 3 | 0 | Pr | NR | Ph | H | H | H | H | —CH3 | |
| 164 | Ir | 3 | 0 | Pr | NR | Ph | H | H | H | H | —C4H9 | |
| 165 | Ir | 3 | 0 | Pr | CR2 | Qn1 | H | H | H | H | —CH3 | —CH3 |
| 166 | Ir | 3 | 0 | Pr | CR2 | Qn2 | H | H | H | H | —C4H9 | —C4H9 |
| 167 | Ir | 3 | 0 | Pr | CR2 | Qx | H | H | H | H | H | —CH3 |
| 168 | Ir | 3 | 0 | Pr | CR2 | Qz1 | — | H | H | H | H | —C4H9 |
| 169 | Ir | 3 | 0 | Pr | CR2 | Ph | H | H | H | CF3 | H | |
| 170 | Ir | 3 | 0 | Pr | CR2 | Ph | H | CF3 | H | H | H | |
| 171 | Ir | 3 | 0 | Pr | CR2 | Ph | H | H | H | CH3 | H | |
| 172 | Ir | 3 | 0 | Pr | CR2 | Ph | H | H | CH3 | H | H | |
| 173 | Ir | 3 | 0 | Pr | CR2 | Qn1 | H | H | H | OCF3 | H | H |
| 174 | Ir | 3 | 0 | Pr | CR2 | Qn2 | H | OC2H5 | H | H | H | H |
| 175 | Ir | 3 | 0 | Pr | CR2 | Qx | H | H | H | OC2H5 | H | H |
| 176 | Ir | 3 | 0 | Pr | CR2 | Qz1 | — | H | COOC2H5 | H | H | H |
| 177 | Ir | 3 | 0 | Pr | O | Ph | H | H | H | CF3 | — | |
| 178 | Ir | 3 | 0 | Pr | O | Ph | H | CF3 | H | H | — | |
| 179 | Ir | 3 | 0 | Pr | NR2 | Ph | H | H | H | CH3 | H | |
| 180 | Ir | 3 | 0 | Pr | NR2 | Ph | H | H | CH3 | H | H | |
| 181 | Ir | 3 | 0 | Pr | NR2 | Qn1 | H | H | H | OCF3 | H | — |
| 182 | Ir | 3 | 0 | Pr | CO | Qn2 | H | OC2H5 | H | H | — | — |
| 183 | Ir | 3 | 0 | Pr | CO | Qx | H | H | H | OC2H5 | — | — |
| 184 | Ir | 3 | 0 | Pr | CO | Qz1 | — | H | COOC2H5 | H | — | — |
| 185 | Rh | 3 | 0 | Pr | CO | Ph | H | H | H | H | | |
| 186 | Rh | 3 | 0 | Pr | CO | Tn1 | H | H | H | H | | |
| 187 | Rh | 3 | 0 | Pr | CR2 | Tn2 | H | H | H | H | H | H |
| 188 | Rh | 3 | 0 | Pr | CR2 | Tn3 | H | H | H | H | H | H |
| 189 | Rh | 3 | 0 | Pr | O | Qn1 | H | H | H | H | | |
| 190 | Rh | 3 | 0 | Pr | O | Qn2 | H | H | H | H | | |
| 191 | Rh | 3 | 0 | Pr | S | Qx | H | H | H | H | | |
| 192 | Rh | 3 | 0 | Pr | S | Qz1 | — | H | H | H | | |
| 193 | Rh | 3 | 0 | Pr | NR | Qz2 | H | — | H | H | H | |
| 194 | Rh | 3 | 0 | Pr | NR | Cn1 | H | H | H | H | H | |
| 195 | Pd | 2 | 0 | Pr | CO | Ph | H | H | H | H | | |
| 196 | Pd | 2 | 0 | Pr | CO | Tn1 | H | H | H | H | | |
| 197 | Pd | 2 | 0 | Pr | CR2 | Tn2 | H | H | H | H | H | H |
| 198 | Pd | 2 | 0 | Pr | CR2 | Tn3 | H | H | H | H | H | H |
| 199 | Pd | 2 | 0 | Pr | O | Qn1 | H | H | H | H | | |
| 200 | Pd | 2 | 0 | Pr | O | Qn2 | H | H | H | H | | |
| 201 | Pd | 2 | 0 | Pr | S | Qx | H | H | H | H | | |
| 202 | Pd | 2 | 0 | Pr | S | Qz1 | — | H | H | H | | |
| 203 | Pd | 2 | 0 | Pr | NR | Qz2 | H | — | H | H | H | |
| 204 | Pd | 2 | 0 | Pr | NR | Cn1 | — | H | H | H | | |
| 205 | Pt | 2 | 0 | Pr | CO | Ph | H | H | H | H | | |
| 206 | Pt | 2 | 0 | Pr | CO | Tn1 | H | H | H | H | | |
| 207 | Pt | 2 | 0 | Pr | CR2 | Tn2 | H | H | H | H | H | H |
| 208 | Pt | 2 | 0 | Pr | CR2 | Tn3 | H | H | H | H | H | H |
| 209 | Pt | 2 | 0 | Pr | O | Qn1 | H | H | H | H | | |
| 210 | Pt | 2 | 0 | Pr | O | Qn2 | H | H | H | H | | |
| 211 | Pt | 2 | 0 | Pr | S | Qx | H | H | H | H | | |
| 212 | Pt | 2 | 0 | Pr | S | Qz1 | — | H | H | H | | |
| 213 | Pt | 2 | 0 | Pr | NR | Qz2 | H | — | H | H | H | |
| 214 | Pt | 3 | 0 | Pr | NR | Cn1 | — | H | H | H | H | |
| 215 | Ir | 2 | 0 | Pr | CR2 | Ph | H | H | H | H | H | H | CH3—CO— |

TABLE 1-continued

| No | M | m | n | | | R1 | R2 | R3 | R4 | | | | | |
|---|---|---|---|---|---|---|---|---|---|---|---|---|---|---|
| 216 | Ir | 2 | 0 | Pr | CR2 | Tn1 | H | H | H | H | H | H | H | CH—CO—CH3<br>CH3—CO—CH—CO—CH3 |
| 217 | Ir | 2 | 0 | Pr | CO | Tn2 | H | H | H | H | | | | CH3—CO—CH—CO—CH3 |
| 218 | Ir | 2 | 0 | Pr | CO | Tn3 | H | H | H | H | | | | CH3—CO—CH—CO—CH3 |

| | | | | L | | | | | | | | | | | | L' | | |
|---|---|---|---|---|---|---|---|---|---|---|---|---|---|---|---|---|---|---|
| No | M | m | n | CyN1 or CyN2 / X | CyC1 or CyC2 | R1 | R2 | R3 | R4 | R5 | R6 | CyN3 | CyC3 | R1 | R2 | R3 | R4 | |
| 219 | Ir | 2 | 1 | Pr | O | Ph | H | H | H | H | | Pr | Tn1 | H | H | H | H |
| 220 | Ir | 2 | 1 | Pr | O | Ph | H | H | H | H | | Pr | Ph | H | H | H | H |
| 221 | Ir | 2 | 1 | Pr | O | Ph | H | H | H | H | | Py1 | Ph | H | H | H | — |
| 222 | Ir | 2 | 1 | Pr | O | Ph | H | H | H | H | | Pr | Ph | CH3 | H | H | H |
| 223 | Ir | 2 | 1 | Pr | O | Ph | H | H | H | H | | Pr | Tn1 | H | H | H | H |
| 224 | Ir | 2 | 1 | Pr | O | Ph | H | H | H | H | | Py1 | Ph | H | H | H | — |
| 225 | Ir | 2 | 1 | Pr | CO | Ph | H | H | H | H | | Pr | Tn1 | H | H | H | H |
| 226 | Ir | 2 | 1 | Pr | CO | Ph | H | H | H | H | | Pr | Ph | H | H | H | H |
| 227 | Ir | 2 | 1 | Pr | CO | Ph | H | H | H | H | | Py1 | Ph | H | H | H | — |
| 228 | Ir | 2 | 1 | Pr | CO | Ph | H | H | H | H | | Pr | Ph | CH3 | H | H | H |
| 229 | Ir | 2 | 1 | Pr | CO | Ph | H | H | H | H | | Pr | Tn1 | H | H | H | H |
| 230 | Ir | 2 | 1 | Pr | CO | Ph | H | H | H | H | | Py1 | Ph | H | H | H | — |
| 231 | Ir | 2 | 1 | Pr | NR | Ph | H | H | H | H | CH3 | Pr | Tn1 | H | H | H | H |
| 232 | Ir | 2 | 1 | Pr | NR | Ph | H | H | H | H | CH3 | Pr | Ph | H | H | H | H |
| 233 | Ir | 2 | 1 | Pr | NR | Ph | H | H | H | H | CH3 | Py1 | Ph | H | H | H | — |
| 234 | Ir | 2 | 1 | Pr | NR | Ph | H | H | H | H | CH3 | Pr | Ph | CF3 | H | H | H |
| 235 | Ir | 2 | 1 | Pr | NR | Ph | H | H | H | H | CH3 | Pr | Tn1 | H | H | H | H |
| 236 | Ir | 2 | 1 | Pr | NR | Ph | H | H | H | H | CH3 | Py1 | Ph | H | H | H | — |
| 237 | Ir | 2 | 1 | Pr | NR | Tn1 | H | H | H | H | C2H5 | Pr | Tn1 | H | H | H | H |
| 238 | Ir | 2 | 1 | Pr | NR | Tn1 | H | H | H | H | C2H5 | Pr | Ph | H | H | H | H |
| 239 | Ir | 2 | 1 | Pr | NR | Tn1 | H | H | H | H | C2H5 | Py1 | Ph | H | H | H | — |
| 240 | Ir | 2 | 1 | Pr | NR | Qn1 | H | H | H | H | C2H5 | Pr | Ph | F | H | H | H |
| 241 | Ir | 2 | 1 | Pr | NR | Qn1 | H | H | H | H | C2H5 | Pr | Tn1 | H | H | H | H |
| 242 | Ir | 2 | 1 | Pr | NR | Qn1 | H | H | H | H | C2H5 | Py1 | Ph | H | H | H | — |
| 243 | Pt | 1 | 1 | Pr | O | Ph | H | H | H | H | | Pr | Tn1 | H | H | H | H |
| 244 | Pt | 1 | 1 | Pr | O | Ph | H | H | H | H | | Pr | Ph | H | H | H | H |
| 245 | Pt | 1 | 1 | Pr | O | Ph | H | H | H | H | | Py1 | Ph | H | H | H | — |
| 246 | Pt | 1 | 1 | Pr | O | Ph | H | H | H | H | | Pr | Ph | CH3 | H | H | H |
| 247 | Pt | 1 | 1 | Pr | O | Ph | H | H | H | H | | Pr | Tn1 | H | H | H | H |
| 248 | Pt | 1 | 1 | Pr | O | Ph | H | H | H | H | | Py1 | Ph | H | H | H | — |
| 249 | Pt | 1 | 1 | Pr | CO | Ph | H | H | H | H | | Pr | Tn1 | H | H | H | H |
| 250 | Pt | 1 | 1 | Pr | CO | Ph | H | H | H | H | | Pr | Ph | H | H | H | H |
| 251 | Pt | 1 | 1 | Pr | CO | Ph | H | H | H | H | | Py1 | Ph | H | H | H | — |
| 252 | Pt | 1 | 1 | Pr | CO | Ph | H | H | H | H | | Pr | Ph | CH3 | H | H | H |
| 253 | Pt | 1 | 1 | Pr | CO | Ph | H | H | H | H | | Pr | Tn1 | H | H | H | H |
| 254 | Pt | 1 | 1 | Pr | CO | Ph | H | H | H | H | | Py1 | Ph | H | H | H | — |
| 255 | Pt | 1 | 1 | Pr | NR | Ph | H | H | H | H | CH3 | Pr | Tn1 | H | H | H | H |
| 256 | Pt | 1 | 1 | Pr | NR | Ph | H | H | H | H | CH3 | Pr | Ph | H | H | H | H |
| 257 | Pt | 1 | 1 | Pr | NR | Ph | H | H | H | H | CH3 | Py1 | Ph | H | H | H | — |
| 258 | Pt | 1 | 1 | Pr | NR | Ph | H | H | H | H | CH3 | Pr | Ph | CF3 | H | H | H |
| 259 | Pt | 1 | 1 | Pr | NR | Ph | H | H | H | H | CH3 | Pr | Tn1 | H | H | H | H |
| 260 | Pt | 1 | 1 | Pr | NR | Ph | H | H | H | H | CH3 | Py1 | Ph | H | H | H | — |
| 261 | Pt | 1 | 1 | Pr | NR | Tn1 | H | H | H | H | C2H5 | Pr | Tn1 | H | H | H | H |
| 262 | Pt | 1 | 1 | Pr | NR | Tn1 | H | H | H | H | C2H5 | Pr | Ph | H | H | H | H |
| 263 | Pt | 1 | 1 | Pr | NR | Tn1 | H | H | H | H | C2H5 | Py1 | Ph | H | H | H | — |
| 264 | Pt | 1 | 1 | Pr | NR | Qn1 | H | H | H | H | C2H5 | Pr | Ph | F | H | H | H |
| 265 | Pt | 1 | 1 | Pr | NR | Qn1 | H | H | H | H | C2H5 | Pr | Tn1 | H | H | H | H |
| 266 | Pt | 1 | 1 | Pr | NR | Qn1 | H | H | H | H | C2H5 | Py1 | Ph | H | H | H | — |
| 267 | Ir | 2 | 1 | Pr | — | Ph | F | H | H | H | | Pr | Ph | CH3 | H | H | H |
| 268 | Ir | 2 | 1 | Pr | — | Ph | F | F | H | H | | Pr | Ph | H | H | H | H |
| 269 | Ir | 2 | 1 | Pr | — | Ph | F | H | H | H | | Pr | Ph | CF3 | H | H | H |
| 270 | Ir | 2 | 1 | Pr | — | Ph | H | H | H | H | | Pr | Tn1 | H | H | H | H |
| 271 | Ir | 2 | 1 | Pr | — | Ph | H | H | H | H | | Pr | Tn2 | H | H | H | H |
| 272 | Ir | 2 | 1 | Pr | — | Ph | H | H | H | H | | Pr | Tn3 | H | H | H | H |
| 273 | Ir | 2 | 1 | Pr | — | Ph | H | H | H | H | | Pr | Np | H | H | H | H |
| 274 | Ir | 2 | 1 | Pr | — | Ph | H | H | H | H | | Pr | Qn1 | H | H | H | H |
| 275 | Ir | 2 | 1 | Pr | — | Ph | H | H | H | H | | Pr | Qn2 | H | H | H | H |
| 276 | Ir | 2 | 1 | Pr | — | Ph | H | H | H | H | | Pr | Qx | H | H | H | H |
| 277 | Ir | 2 | 1 | Pr | — | Ph | H | H | H | H | | Pr | Qz1 | — | H | H | H |

TABLE 1-continued

| | | | | | | | | | | | | | | | | | |
|---|---|---|---|---|---|---|---|---|---|---|---|---|---|---|---|---|---|
| 278 | Ir | 2 | 1 | Pr | — | Ph | H | H | H | H | Pr | Qz2 | H | — | H | H |
| 279 | Ir | 2 | 1 | Pr | — | Ph | H | H | H | H | Pr | Cn1 | — | H | H | H |
| 280 | Ir | 2 | 1 | Pr | — | Ph | H | H | H | H | Pr | Cn2 | H | — | H | H |
| 281 | Ir | 2 | 1 | Pr | — | Ph | H | H | H | H | Pr | Pz | — | — | H | H |
| 282 | Ir | 2 | 1 | Pr | — | Ph | H | H | H | H | Pr | Ph | CH3 | H | H | H |
| 283 | Ir | 2 | 1 | Pr | — | Ph | H | H | H | H | Pr | Ph | H | CF3 | H | H |
| 284 | Ir | 2 | 1 | Pr | — | Ph | H | H | H | H | Pr | tn3 | H | H | H | CF3 |
| 285 | Ir | 1 | 2 | Pr | — | Ph | H | H | H | H | Pr | Tn1 | H | H | H | H |
| 286 | Ir | 1 | 2 | Pr | — | Ph | H | H | H | H | Pr | Tn2 | H | H | H | H |
| 287 | Ir | 1 | 2 | Pr | — | Ph | H | H | H | H | Pr | Tn3 | H | H | H | H |
| 288 | Ir | 1 | 2 | Pr | — | Ph | H | H | H | H | Pr | Np | H | H | H | H |
| 289 | Ir | 1 | 2 | Pr | — | Ph | H | H | H | H | Pr | Qn1 | H | H | H | H |
| 290 | Ir | 1 | 2 | Pr | — | Ph | H | H | H | H | Pr | Qn2 | H | H | H | H |
| 291 | Ir | 1 | 2 | Pr | — | Ph | H | H | H | H | Pr | Qx | H | H | H | H |
| 292 | Ir | 1 | 2 | Pr | — | Ph | H | H | H | H | Pr | Qx1 | — | H | H | H |
| 293 | Ir | 1 | 2 | Pr | — | Ph | H | H | H | H | Pr | Qx2 | H | — | H | H |
| 294 | Ir | 1 | 2 | Pr | — | Ph | H | H | H | H | Pr | Cn1 | — | H | H | H |
| 295 | Ir | 1 | 2 | Pr | — | Ph | H | H | H | H | Pr | Cn2 | H | — | H | H |
| 296 | Ir | 1 | 2 | Pr | — | Ph | H | H | H | H | Pr | Pz | — | — | H | H |
| 297 | Ir | 1 | 2 | Pr | — | Ph | H | H | H | H | Pr | Ph | CH3 | H | H | H |
| 298 | Ir | 1 | 2 | Pr | — | Ph | H | H | H | H | Pr | Ph | H | CF3 | H | H |
| 299 | Ir | 1 | 2 | Pr | — | Ph | H | H | H | H | Pr | tn3 | H | H | H | CF3 |
| 300 | Ir | 2 | 1 | Pr | — | Tn1 | H | H | H | H | Pr | Tn3 | H | H | H | H |
| 301 | Ir | 2 | 1 | Pr | — | Tn1 | H | H | H | H | Pr | Np | H | H | H | H |
| 302 | Ir | 2 | 1 | Pr | — | Tn1 | H | H | H | H | Pr | Qn1 | H | H | H | H |
| 303 | Ir | 2 | 1 | Pr | — | Tn1 | H | H | H | H | Pr | Qn2 | H | H | H | H |
| 304 | Ir | 2 | 1 | Pr | — | Tn1 | H | H | H | H | Pr | Qx | H | H | H | H |
| 305 | Ir | 2 | 1 | Pr | — | Tn1 | H | H | H | H | Pr | Qz1 | — | H | H | H |
| 306 | Ir | 2 | 1 | Pr | — | Tn1 | H | H | H | H | Pr | Qz2 | H | — | H | H |
| 307 | Ir | 2 | 1 | Pr | — | Tn1 | H | H | H | H | Pr | Cn1 | — | H | H | H |
| 308 | Ir | 2 | 1 | Pr | — | Tn1 | H | H | H | H | Pr | Cn2 | H | — | H | H |
| 309 | Ir | 2 | 1 | Pr | — | Tn1 | H | H | H | H | Pr | Pz | — | — | H | H |
| 310 | Ir | 2 | 1 | Pr | — | Tn1 | H | H | H | H | Pr | Ph | CH3 | H | H | H |
| 311 | Ir | 2 | 1 | Pr | — | Tn1 | H | H | H | H | Pr | Ph | H | CF3 | H | H |
| 312 | Ir | 2 | 1 | Pr | — | Tn1 | H | H | H | H | Pr | tn3 | H | H | H | CF3 |
| 313 | Ir | 1 | 2 | Pr | — | Tn1 | H | H | H | H | Pr | Tn3 | H | H | H | H |
| 314 | Ir | 1 | 2 | Pr | — | Tn1 | H | H | H | H | Pr | Np | H | H | H | H |
| 315 | Ir | 1 | 2 | Pr | — | Tn1 | H | H | H | H | Pr | Qn1 | H | H | H | H |
| 316 | Ir | 1 | 2 | Pr | — | Tn1 | H | H | H | H | Pr | Qn2 | H | H | H | H |
| 317 | Ir | 1 | 2 | Pr | — | Tn1 | H | H | H | H | Pr | Qx | H | H | H | H |
| 318 | Ir | 1 | 2 | Pr | — | Tn1 | H | H | H | H | Pr | Qz1 | — | H | H | H |
| 319 | Ir | 1 | 2 | Pr | — | Tn1 | H | H | H | H | Pr | Qz2 | H | — | H | H |
| 320 | Ir | 1 | 2 | Pr | — | Tn1 | H | H | H | H | Pr | Cn1 | — | H | H | H |
| 321 | Ir | 1 | 2 | Pr | — | Tn1 | H | H | H | H | Pr | Cn2 | H | — | H | H |
| 322 | Ir | 1 | 2 | Pr | — | Tn1 | H | H | H | H | Pr | Pz | — | — | H | H |
| 323 | Ir | 1 | 2 | Pr | — | Tn1 | H | H | H | H | Pr | Ph | CH3 | H | H | H |
| 324 | Ir | 1 | 2 | Pr | — | Tn1 | H | H | H | H | Pr | Ph | H | CF3 | H | H |
| 325 | Ir | 1 | 2 | Pr | — | Tn1 | H | H | H | H | Pr | tn3 | H | H | H | CF3 |
| 326 | Ir | 2 | 1 | Py1 | — | Ph | H | H | H | H | Pr | Tn1 | H | H | H | H |
| 327 | Ir | 2 | 1 | Py1 | — | Ph | H | H | H | H | Pr | Tn1 | H | H | H | H |
| 328 | Ir | 2 | 1 | Py1 | — | Ph | H | H | H | H | Pr | Tn3 | H | H | H | H |
| 329 | Ir | 2 | 1 | Py1 | — | Ph | H | H | H | H | Pr | Np | H | H | H | H |
| 330 | Ir | 2 | 1 | Py1 | — | Ph | H | H | H | H | Pr | Qn1 | H | H | H | H |
| 331 | Ir | 2 | 1 | Py1 | — | Ph | H | H | H | H | Pr | Qn2 | H | H | H | H |
| 332 | Ir | 2 | 1 | Py1 | — | Ph | H | H | H | H | Pr | Qx | H | H | H | H |
| 333 | Ir | 2 | 1 | Py1 | — | Ph | H | H | H | H | Pr | Qz1 | — | H | H | H |
| 334 | Ir | 2 | 1 | Py1 | — | Ph | H | H | H | H | Pr | Qz2 | H | — | H | H |
| 335 | Ir | 2 | 1 | Py1 | — | Ph | H | H | H | H | Pr | Cn1 | — | H | H | H |
| 336 | Ir | 2 | 1 | Py1 | — | Ph | H | H | H | H | Pr | Cn2 | H | — | H | H |
| 337 | Ir | 2 | 1 | Py1 | — | Ph | H | H | H | H | Pr | Pz | — | — | H | H |
| 338 | Ir | 2 | 1 | Py1 | — | Ph | H | H | H | H | Pr | Ph | CH3 | H | H | H |
| 339 | Ir | 2 | 1 | Py1 | — | Ph | H | H | H | H | Pr | Ph | H | CF3 | H | H |
| 340 | Ir | 2 | 1 | Py1 | — | Ph | H | H | H | H | Pr | tn3 | H | H | H | CF3 |
| 341 | Ir | 1 | 2 | Py1 | — | Ph | H | H | H | H | Pr | Tn1 | H | H | H | H |
| 342 | Ir | 1 | 2 | Py1 | — | Ph | H | H | H | H | Pr | Tn2 | H | H | H | H |
| 343 | Ir | 1 | 2 | Py1 | — | Ph | H | H | H | H | Pr | Tn3 | H | H | H | H |
| 344 | Ir | 1 | 2 | Py1 | — | Ph | H | H | H | H | Pr | Np | H | H | H | H |
| 345 | Ir | 1 | 2 | Py1 | — | Ph | H | H | H | H | Pr | Qn1 | H | H | H | H |
| 346 | Ir | 1 | 2 | Py1 | — | Ph | H | H | H | H | Pr | Qn2 | H | H | H | H |
| 347 | Ir | 1 | 2 | Py1 | — | Ph | H | H | H | H | Pr | Qx | H | H | H | H |
| 348 | Ir | 1 | 2 | Py1 | — | Pr | H | H | H | H | Pr | Qz1 | — | H | H | H |
| 349 | Ir | 1 | 2 | Py1 | — | Pr | H | H | H | H | Pr | Qz2 | H | — | H | H |
| 350 | Ir | 1 | 2 | Py1 | — | Pr | H | H | H | H | Pr | Cn1 | — | H | H | H |
| 351 | Ir | 1 | 2 | Py1 | — | Pr | H | H | H | H | Pr | Cn2 | H | — | H | H |
| 352 | Ir | 1 | 2 | Py1 | — | Pr | H | H | H | H | Pr | Pz | — | — | H | H |
| 353 | Ir | 1 | 2 | Py1 | — | Pr | H | H | H | H | Pr | Ph | CH3 | H | H | H |
| 354 | Ir | 1 | 2 | Py1 | — | Pr | H | H | H | H | Pr | Ph | H | CF3 | H | H |
| 355 | Ir | 1 | 2 | Py1 | — | Pr | H | H | H | H | Pr | tn3 | H | H | H | CF3 |
| 356 | Ir | 2 | 1 | Py1 | — | Ph | H | H | H | H | Pz | Tn1 | H | H | H | H |

TABLE 1-continued

| | | | | | | | | | | | | | | | | | |
|---|---|---|---|---|---|---|---|---|---|---|---|---|---|---|---|---|---|
| 357 | Ir | 2 | 1 | Py1 | — | Ph | H | H | H | H | Pz | Tn2 | H | H | H | H |
| 358 | Ir | 2 | 1 | Py1 | — | Ph | H | H | H | H | Pz | Tn3 | H | H | H | H |
| 359 | Ir | 2 | 1 | Py1 | — | Ph | H | H | H | H | Pa | Np | H | H | — | H |
| 360 | Ir | 2 | 1 | Py1 | — | Ph | H | H | H | H | Pa | Qn1 | H | H | — | H |
| 361 | Ir | 2 | 1 | Py1 | — | Ph | H | H | H | H | Pa | Qn2 | H | H | — | H |
| 362 | Ir | 2 | 1 | Py1 | — | Ph | H | H | H | H | Py2 | Qx | H | H | H | H |
| 363 | Ir | 2 | 1 | Py1 | — | Ph | H | H | H | H | Py2 | Qz1 | H | — | H | H |
| 364 | Ir | 2 | 1 | Py1 | — | Ph | H | H | H | H | Py2 | Qz2 | H | — | H | H |
| 365 | Ir | 2 | 1 | Py1 | — | Ph | H | H | H | H | Py1 | Cn1 | — | H | H | H |
| 366 | Ir | 2 | 1 | Py1 | — | Ph | H | H | H | H | Py1 | Cn2 | H | — | H | H |
| 367 | Ir | 2 | 1 | Py1 | — | Ph | H | H | H | H | Py1 | Pz | — | — | H | H |
| 368 | Ir | 2 | 1 | Py1 | — | Ph | H | H | H | H | Py2 | Ph | CH3 | H | H | H |
| 369 | Ir | 2 | 1 | Py1 | — | Ph | H | H | H | H | Py2 | Ph | H | CF3 | H | H |
| 370 | Ir | 2 | 1 | Py1 | — | Ph | H | H | H | H | Py2 | tn3 | H | H | H | CF3 |
| 371 | Ir | 2 | 1 | Pr | — | Ph | H | H | H | H | formula 11 | | | | | |
| 372 | Ir | 2 | 1 | Pr | — | Ph | H | H | H | H | formula 12 | | | | | |
| 373 | Ir | 2 | 1 | Pr | — | Ph | H | H | H | H | formula 13 | | | | | |
| 374 | Ir | 2 | 1 | Pr | — | Ph | H | H | H | H | formula 14 | | | | | |
| 375 | Ir | 2 | 1 | Pr | — | Tn1 | H | H | H | H | formula 11 | | | | | |
| 376 | Ir | 2 | 1 | Pr | — | Tn1 | H | H | H | H | formula 12 | | | | | |
| 377 | Ir | 2 | 1 | Pr | — | Tn1 | H | H | H | H | formula 13 | | | | | |
| 378 | Ir | 2 | 1 | Pr | — | Tn1 | H | H | H | H | formula 14 | | | | | |
| 379 | Ir | 2 | 1 | Pr | — | Tn3 | H | H | H | H | formula 11 | | | | | |
| 380 | Ir | 2 | 1 | Pr | — | Tn3 | H | H | H | H | formula 12 | | | | | |
| 381 | Ir | 2 | 1 | Pr | — | Tn3 | H | H | H | H | formula 13 | | | | | |
| 382 | Ir | 2 | 1 | Pr | — | Tn3 | H | H | H | H | formula 14 | | | | | |
| 383 | Ir | 2 | 1 | Pr | — | Np | H | H | H | H | formula 11 | | | | | |
| 384 | Ir | 2 | 1 | Pr | — | Np | H | H | H | H | formula 12 | | | | | |
| 385 | Ir | 2 | 1 | Pr | — | Np | H | H | H | H | formula 13 | | | | | |
| 386 | Ir | 2 | 1 | Pr | — | Np | H | H | H | H | formula 14 | | | | | |
| 387 | Ir | 2 | 1 | Pr | — | Qn2 | H | H | H | H | formula 11 | | | | | |
| 388 | Ir | 2 | 1 | Pr | — | Qn2 | H | H | H | H | formula 12 | | | | | |
| 389 | Ir | 2 | 1 | Pr | — | Qn2 | H | H | H | H | formula 13 | | | | | |
| 390 | Ir | 2 | 1 | Pr | — | Qn2 | H | H | H | H | formula 14 | | | | | |
| 391 | Ir | 2 | 1 | Py1 | — | Ph | H | H | H | — | formula 11 | | | | | |
| 392 | Ir | 2 | 1 | Py1 | — | Ph | H | H | H | — | formula 12 | | | | | |
| 393 | Ir | 2 | 1 | Py1 | — | Ph | H | H | H | — | formula 13 | | | | | |
| 394 | Ir | 2 | 1 | Py1 | — | Ph | H | H | H | — | formula 14 | | | | | |
| 395 | Ir | 2 | 1 | Py2 | — | Ph | H | H | H | H | formula 11 | | | | | |
| 396 | Ir | 2 | 1 | Py2 | — | Ph | H | H | H | H | formula 12 | | | | | |
| 397 | Ir | 2 | 1 | Py2 | — | Ph | H | H | H | H | formula 13 | | | | | |
| 398 | Ir | 2 | 1 | Py2 | — | Ph | H | H | H | H | formula 14 | | | | | |
| 399 | Ir | 2 | 1 | Pz | — | Ph | H | H | H | H | formula 11 | | | | | |
| 400 | Ir | 2 | 1 | Pz | — | Ph | H | H | H | H | formula 12 | | | | | |
| 401 | Ir | 2 | 1 | Pz | — | Ph | H | H | H | H | formula 13 | | | | | |
| 402 | Ir | 2 | 1 | Pz | — | Ph | H | H | H | H | formula 14 | | | | | |
| 403 | Ir | 2 | 1 | Pa | — | Ph | H | H | — | H | formula 11 | | | | | |
| 404 | Ir | 2 | 1 | Pa | — | Ph | H | H | — | H | formula 12 | | | | | |
| 405 | Ir | 2 | 1 | Pa | — | Ph | H | H | — | H | formula 13 | | | | | |
| 406 | Ir | 2 | 1 | pa | — | Ph | H | H | — | H | formula 14 | | | | | |
| 407 | Ir | 1 | 2 | Pr | — | Ph | H | H | H | H | formula 11 | | | | | |
| 408 | Ir | 1 | 2 | Pr | — | Ph | H | H | H | H | formula 12 | | | | | |
| 409 | Ir | 1 | 2 | Pr | — | Ph | H | H | H | H | formula 13 | | | | | |
| 410 | Ir | 1 | 2 | Pr | — | Ph | H | H | H | H | formula 14 | | | | | |
| 411 | Ir | 1 | 2 | Pr | — | Tn1 | H | H | H | H | formula 11 | | | | | |
| 412 | Ir | 1 | 2 | Pr | — | Tn1 | H | H | H | H | formula 12 | | | | | |
| 413 | Ir | 1 | 2 | Pr | — | Tn1 | H | H | H | H | formula 13 | | | | | |
| 414 | Ir | 1 | 2 | Pr | — | Tn1 | H | H | H | H | formula 14 | | | | | |
| 415 | Ir | 1 | 2 | Pr | — | Tn3 | H | H | H | H | formula 11 | | | | | |
| 416 | Ir | 1 | 2 | Pr | — | Tn3 | H | H | H | H | formula 12 | | | | | |
| 417 | Ir | 1 | 2 | Pr | — | Tn3 | H | H | H | H | formula 13 | | | | | |
| 418 | Ir | 1 | 2 | Pr | — | Tn3 | H | H | H | H | formula 14 | | | | | |
| 419 | Ir | 1 | 2 | Pr | — | Np | H | H | H | H | formula 11 | | | | | |
| 420 | Ir | 1 | 2 | Pr | — | Np | H | H | H | H | formula 12 | | | | | |
| 421 | Ir | 1 | 2 | Pr | — | Np | H | H | H | H | formula 13 | | | | | |
| 422 | Ir | 1 | 2 | Pr | — | Np | H | H | H | H | formula 14 | | | | | |
| 423 | Ir | 1 | 2 | Pr | — | Qn2 | H | H | H | H | formula 11 | | | | | |
| 424 | Ir | 1 | 2 | Pr | — | Qn2 | H | H | H | H | formula 12 | | | | | |
| 425 | Ir | 1 | 2 | Pr | — | Qn2 | H | H | H | H | formula 13 | | | | | |
| 426 | Ir | 1 | 2 | Pr | — | Qn2 | H | H | H | H | formula 14 | | | | | |
| 427 | Ir | 1 | 2 | Py1 | — | Ph | H | H | H | — | formula 11 | | | | | |
| 428 | Ir | 1 | 2 | Py1 | — | Ph | H | H | H | — | formula 12 | | | | | |
| 429 | Ir | 1 | 2 | Py1 | — | Ph | H | H | H | — | formula 13 | | | | | |
| 430 | Ir | 1 | 2 | Py1 | — | Ph | H | H | H | — | formula 14 | | | | | |
| 431 | Ir | 1 | 2 | Py2 | — | Ph | H | H | H | H | formula 11 | | | | | |
| 432 | Ir | 1 | 2 | Py2 | — | Ph | H | H | H | H | formula 12 | | | | | |
| 433 | Ir | 1 | 2 | Py2 | — | Ph | H | H | H | H | formula 13 | | | | | |
| 434 | Ir | 1 | 2 | Py2 | — | Ph | H | H | H | H | formula 14 | | | | | |
| 435 | Ir | 1 | 2 | Pz | — | Ph | H | H | H | H | formula 11 | | | | | |

TABLE 1-continued

| | | | | | | | | | | | | | | | | | | |
|---|---|---|---|---|---|---|---|---|---|---|---|---|---|---|---|---|---|---|
| 436 | Ir | 1 | 2 | Pz | — | Ph | H | H | H | H | | | | | | formula 12 | | |
| 437 | Ir | 1 | 2 | Pz | — | Ph | H | H | H | H | | | | | | formula 13 | | |
| 438 | Ir | 1 | 2 | Pz | — | Ph | H | H | H | H | | | | | | formula 14 | | |
| 439 | Ir | 1 | 2 | Pa | — | Ph | H | H | — | H | | | | | | formula 11 | | |
| 440 | Ir | 1 | 2 | Pa | — | Ph | H | H | — | H | | | | | | formula 12 | | |
| 441 | Ir | 1 | 2 | Pa | — | Ph | H | H | — | H | | | | | | formula 13 | | |
| 442 | Ir | 1 | 2 | Pa | — | Ph | H | H | — | H | | | | | | formula 14 | | |
| 443 | Rh | 2 | 1 | Pr | — | Ph | H | H | H | H | Pr | Tn1 | H | H | H | H | | |
| 444 | Rh | 2 | 1 | Pr | — | Ph | H | H | H | H | Pr | Tn2 | H | H | H | H | | |
| 445 | Rh | 2 | 1 | Pr | — | Ph | H | H | H | H | Pr | Tn3 | H | H | H | H | | |
| 446 | Rh | 2 | 1 | Pr | — | Ph | H | H | H | H | Pr | Np | H | H | H | H | | |
| 447 | Rh | 2 | 1 | Pr | — | Ph | H | H | H | H | Pr | Qn1 | H | H | H | H | | |
| 448 | Rh | 2 | 1 | Pr | — | Ph | H | H | H | H | Pr | Qn2 | H | H | H | H | | |
| 449 | Rh | 2 | 1 | Pr | — | Ph | H | H | H | H | Pr | Qx | H | H | H | H | | |
| 450 | Rh | 2 | 1 | Pr | — | Ph | H | H | H | H | Pr | Qz1 | — | H | H | H | | |
| 451 | Rh | 2 | 1 | Pr | — | Ph | H | H | H | H | Pr | Qz2 | H | — | H | H | | |
| 452 | Rh | 2 | 1 | Pr | — | Ph | H | H | H | H | Pr | Cn1 | — | H | H | H | | |
| 453 | Rh | 2 | 1 | Pr | — | Ph | H | H | H | H | Pr | Cn2 | H | — | H | H | | |
| 454 | Rh | 2 | 1 | Pr | — | Ph | H | H | H | H | Pr | Pz | — | — | H | H | | |
| 455 | Rh | 2 | 1 | Pr | — | Ph | H | H | H | H | Pr | Ph | CH3 | H | H | H | | |
| 456 | Rh | 2 | 1 | Pr | — | Ph | H | H | H | H | Pr | Ph | H | CF3 | H | H | | |
| 457 | Rh | 2 | 1 | Pr | — | Ph | H | H | H | H | Pr | tn3 | H | H | H | CF3 | | |
| 458 | Rh | 1 | 2 | Pr | — | Ph | H | H | H | H | Pr | Tn1 | H | H | H | H | | |
| 459 | Rh | 1 | 2 | Pr | — | Ph | H | H | H | H | Pr | Tn2 | H | H | H | H | | |
| 460 | Rh | 1 | 2 | Pr | — | Ph | H | H | H | H | Pr | Tn3 | H | H | H | H | | |
| 461 | Rh | 1 | 2 | Pr | — | Ph | H | H | H | H | Pr | Np | H | H | H | H | | |
| 462 | Rh | 1 | 2 | Pr | — | Ph | H | H | H | H | Pr | Qn1 | H | H | H | H | | |
| 463 | Rh | 1 | 2 | Pr | — | Ph | H | H | H | H | Pr | Qn2 | H | H | H | H | | |
| 464 | Rh | 1 | 2 | Pr | — | Ph | H | H | H | H | Pr | Qx | H | H | H | H | | |
| 465 | Rh | 1 | 2 | Pr | — | Ph | H | H | H | H | Pr | Qz1 | — | H | H | H | | |
| 466 | Rh | 1 | 2 | Pr | — | Ph | H | H | H | H | Pr | Qz2 | H | — | H | H | | |
| 467 | Rh | 1 | 2 | Pr | — | Ph | H | H | H | H | Pr | Cn1 | — | H | H | H | | |
| 468 | Rh | 1 | 2 | Pr | — | Ph | H | H | H | H | Pr | Cn2 | H | — | H | H | | |
| 469 | Rh | 1 | 2 | Pr | — | Ph | H | H | H | H | Pr | Pz | — | — | H | H | | |
| 470 | Rh | 1 | 2 | Pr | — | Ph | H | H | H | H | Pr | Ph | CH3 | H | H | H | | |
| 471 | Rh | 1 | 2 | Pr | — | Ph | H | H | H | H | Pr | Ph | H | CF3 | H | H | | |
| 472 | Rh | 1 | 2 | Pr | — | Ph | H | H | H | H | Pr | tn3 | H | H | H | CF3 | | |
| 473 | Rh | 2 | 1 | Pr | — | Tn1 | H | H | H | H | Pr | Tn3 | H | H | H | H | | |
| 474 | Rh | 2 | 1 | Pr | — | Tn1 | H | H | H | H | Pr | Np | H | H | H | H | | |
| 475 | Rh | 2 | 1 | Pr | — | Tn1 | H | H | H | H | Pr | Qn1 | H | H | H | H | | |
| 476 | Rh | 2 | 1 | Pr | — | Tn1 | H | H | H | H | Pr | Qn2 | H | H | H | H | | |
| 477 | Rh | 2 | 1 | Pr | — | Tn1 | H | H | H | H | Pr | Qx | H | H | H | H | | |
| 478 | Rh | 2 | 1 | Pr | — | Tn1 | H | H | H | H | Pr | Qz1 | — | H | H | H | | |
| 479 | Rh | 2 | 1 | Pr | — | Tn1 | H | H | H | H | Pr | Qz2 | H | — | H | H | | |
| 480 | Rh | 2 | 1 | Pr | — | Tn1 | H | H | H | H | Pr | Cn1 | — | H | H | H | | |
| 481 | Rh | 2 | 1 | Pr | — | Tn1 | H | H | H | H | Pr | Qn2 | H | — | H | H | | |
| 482 | Rh | 2 | 1 | Pr | — | Tn1 | H | H | H | H | Pr | Pz | — | — | H | H | | |
| 483 | Rh | 2 | 1 | Pr | — | Tn1 | H | H | H | H | Pr | Ph | CH3 | H | H | H | | |
| 484 | Rh | 2 | 1 | Pr | — | Tn1 | H | H | H | H | Pr | Ph | H | CF3 | H | H | | |
| 485 | Rh | 2 | 1 | Pr | — | Tn1 | H | H | H | H | Pr | tn3 | H | H | H | CF3 | | |
| 486 | Rh | 1 | 2 | Pr | — | Tn1 | H | H | H | H | Pr | Tn3 | H | H | H | H | | |
| 487 | Rh | 1 | 2 | Pr | — | Tn1 | H | H | H | H | Pr | Np | H | H | H | H | | |
| 488 | Rh | 1 | 2 | Pr | — | Tn1 | H | H | H | H | Pr | Qn1 | H | H | H | H | | |
| 489 | Rh | 1 | 2 | Pr | — | Tn1 | H | H | H | H | Pr | Qn2 | H | H | H | H | | |
| 490 | Rh | 1 | 2 | Pr | — | Tn1 | H | H | H | H | Pr | Qx | H | H | H | H | | |
| 491 | Rh | 1 | 2 | Pr | — | Tn1 | H | H | H | H | Pr | Qz1 | — | H | H | H | | |
| 492 | Rh | 1 | 2 | Pr | — | Tn1 | H | H | H | H | Pr | Qz2 | H | — | H | H | | |
| 493 | Rh | 1 | 2 | Pr | — | Tn1 | H | H | H | H | Pr | Cr1 | — | H | H | H | | |
| 494 | Rh | 1 | 2 | Pr | — | Tn1 | H | H | H | H | Pr | Cn2 | H | — | H | H | | |
| 495 | Rh | 1 | 2 | Pr | — | Tn1 | H | H | H | H | Pr | Pz | — | — | H | H | | |
| 496 | Rh | 1 | 2 | Pr | — | Tn1 | H | H | H | H | Pr | Ph | CH3 | H | H | H | | |
| 497 | Rh | 1 | 2 | Pr | — | Tn1 | H | H | H | H | Pr | Ph | H | CF3 | H | H | | |
| 498 | Rh | 1 | 2 | Pr | — | Tn1 | H | H | H | H | Pr | tn3 | H | H | H | CF3 | | |
| 499 | Rh | 2 | 1 | Pr | — | Ph | H | H | H | H | | | | | | formula 11 | | |
| 500 | Rh | 2 | 1 | Pr | — | Ph | H | H | H | H | | | | | | formula 12 | | |
| 501 | Rh | 2 | 1 | Pr | — | Ph | H | H | H | H | | | | | | formula 13 | | |
| 502 | Rh | 2 | 1 | Pr | — | Ph | H | H | H | H | | | | | | formula 14 | | |
| 503 | Rh | 2 | 1 | Pr | — | Tn1 | H | H | H | H | | | | | | formula 11 | | |
| 504 | Rh | 2 | 1 | Pr | — | Tn1 | H | H | H | H | | | | | | formula 12 | | |
| 505 | Rh | 2 | 1 | Pr | — | Tn1 | H | H | H | H | | | | | | formula 13 | | |
| 506 | Rh | 2 | 1 | Pr | — | Tn1 | H | H | H | H | | | | | | formula 14 | | |
| 507 | Rh | 2 | 1 | Pr | — | Tn3 | H | H | H | H | | | | | | formula 11 | | |
| 508 | Rh | 2 | 1 | Pr | — | Tn3 | H | H | H | H | | | | | | formula 12 | | |
| 509 | Rh | 2 | 1 | Pr | — | Tn3 | H | H | H | H | | | | | | formula 13 | | |
| 510 | Rh | 2 | 1 | Pr | — | Tn3 | H | H | H | H | | | | | | formula 14 | | |
| 511 | Rh | 2 | 1 | Pr | — | Np | H | H | H | H | | | | | | formula 11 | | |
| 512 | Rh | 2 | 1 | Pr | — | Np | H | H | H | H | | | | | | formula 12 | | |
| 513 | Rh | 2 | 1 | Pr | — | Np | H | H | H | H | | | | | | formula 13 | | |
| 514 | Rh | 2 | 1 | Pr | — | Np | H | H | H | H | | | | | | formula 14 | | |

TABLE 1-continued

| | | | | | | | | | | | | | | | | | | | |
|---|---|---|---|---|---|---|---|---|---|---|---|---|---|---|---|---|---|---|---|
| 515 | Rh | 2 | 1 | Pr | — | Qn2 | H | H | H | H | | | | | | formula 11 | | | |
| 516 | Rh | 2 | 1 | Pr | — | Qn2 | H | H | H | H | | | | | | formula 12 | | | |
| 517 | Rh | 2 | 1 | Pr | — | Qn2 | H | H | H | H | | | | | | formula 13 | | | |
| 518 | Rh | 2 | 1 | Pr | — | Qn2 | H | H | H | H | | | | | | formula 14 | | | |
| 519 | Rh | 2 | 1 | Py1 | — | Ph | H | H | H | — | | | | | | formula 11 | | | |
| 520 | Rh | 2 | 1 | Py1 | — | Ph | H | H | H | — | | | | | | formula 12 | | | |
| 521 | Rh | 2 | 1 | Py1 | — | Ph | H | H | H | — | | | | | | formula 13 | | | |
| 522 | Rh | 2 | 1 | Py1 | — | Ph | H | H | H | — | | | | | | formula 14 | | | |
| 523 | Rh | 2 | 1 | Py2 | — | Ph | H | H | H | H | | | | | | formula 11 | | | |
| 524 | Rh | 2 | 1 | Py2 | — | Ph | H | H | H | H | | | | | | formula 12 | | | |
| 525 | Rh | 2 | 1 | Py2 | — | Ph | H | H | H | H | | | | | | formula 13 | | | |
| 526 | Rh | 2 | 1 | Py2 | — | Ph | H | H | H | H | | | | | | formula 14 | | | |
| 527 | Rh | 2 | 1 | Pz | — | Ph | H | H | H | H | | | | | | formula 11 | | | |
| 528 | Rh | 2 | 1 | Pz | — | Ph | H | H | H | H | | | | | | formula 12 | | | |
| 529 | Rh | 2 | 1 | Pz | — | Ph | H | H | H | H | | | | | | formula 13 | | | |
| 530 | Rh | 2 | 1 | Pz | — | Ph | H | H | H | H | | | | | | formula 14 | | | |
| 531 | Rh | 2 | 1 | Pa | — | Ph | H | H | — | H | | | | | | formula 11 | | | |
| 532 | Rh | 2 | 1 | Pa | — | Ph | H | H | — | H | | | | | | formula 12 | | | |
| 533 | Rh | 2 | 1 | Pa | — | Ph | H | H | — | H | | | | | | formula 13 | | | |
| 534 | Rh | 2 | 1 | Pa | — | Ph | H | H | — | H | | | | | | formula 14 | | | |
| 535 | Rh | 1 | 2 | Pr | — | Ph | H | H | H | H | | | | | | formula 11 | | | |
| 536 | Rh | 1 | 2 | Pr | — | Ph | H | H | H | H | | | | | | formula 12 | | | |
| 537 | Rh | 1 | 2 | Pr | — | Ph | H | H | H | H | | | | | | formula 13 | | | |
| 538 | Rh | 1 | 2 | Pr | — | Ph | H | H | H | H | | | | | | formula 14 | | | |
| 539 | Rh | 1 | 2 | Pr | — | Tn1 | H | H | H | H | | | | | | formula 11 | | | |
| 540 | Rh | 1 | 2 | Pr | — | Tn1 | H | H | H | H | | | | | | formula 12 | | | |
| 541 | Rh | 1 | 2 | Pr | — | Tn1 | H | H | H | H | | | | | | formula 13 | | | |
| 542 | Rh | 1 | 2 | Pr | — | Tn1 | H | H | H | H | | | | | | formula 14 | | | |
| 543 | Rh | 1 | 2 | Pr | — | Tn3 | H | H | H | H | | | | | | formula 11 | | | |
| 544 | Rh | 1 | 2 | Pr | — | Tn3 | H | H | H | H | | | | | | formula 12 | | | |
| 545 | Rh | 1 | 2 | Pr | — | Tn3 | H | H | H | H | | | | | | formula 13 | | | |
| 546 | Rh | 1 | 2 | Pr | — | Tn3 | H | H | H | H | | | | | | formula 14 | | | |
| 547 | Rh | 1 | 2 | Pr | — | Np | H | H | H | H | | | | | | formula 11 | | | |
| 548 | Rh | 1 | 2 | Pr | — | Np | H | H | H | H | | | | | | formula 12 | | | |
| 549 | Rh | 1 | 2 | Pr | — | Np | H | H | H | H | | | | | | formula 13 | | | |
| 550 | Rh | 1 | 2 | Pr | — | Np | H | H | H | H | | | | | | formula 14 | | | |
| 551 | Rh | 1 | 2 | Pr | — | Qn2 | H | H | H | H | | | | | | formula 11 | | | |
| 552 | Rh | 1 | 2 | Pr | — | Qn2 | H | H | H | H | | | | | | formula 12 | | | |
| 553 | Rh | 1 | 2 | Pr | — | Qn2 | H | H | H | H | | | | | | formula 13 | | | |
| 554 | Rh | 1 | 2 | Pr | — | Qn2 | H | H | H | H | | | | | | formula 14 | | | |
| 555 | Rh | 1 | 2 | Py1 | — | Ph | H | H | H | — | | | | | | formula 11 | | | |
| 556 | Rh | 1 | 2 | Py1 | — | Ph | H | H | H | — | | | | | | formula 12 | | | |
| 557 | Rh | 1 | 2 | Py1 | — | Ph | H | H | H | — | | | | | | formula 13 | | | |
| 558 | Rh | 1 | 2 | Py1 | — | Ph | H | H | H | — | | | | | | formula 14 | | | |
| 559 | Rh | 1 | 2 | Py2 | — | Ph | H | H | H | H | | | | | | formula 11 | | | |
| 560 | Rh | 1 | 2 | Py2 | — | Ph | H | H | H | H | | | | | | formula 12 | | | |
| 561 | Rh | 1 | 2 | Py2 | — | Ph | H | H | H | H | | | | | | formula 13 | | | |
| 562 | Rh | 1 | 2 | Py2 | — | Ph | H | H | H | H | | | | | | formula 14 | | | |
| 563 | Rh | 1 | 2 | Pz | — | Ph | H | H | H | H | | | | | | formula 11 | | | |
| 564 | Rh | 1 | 2 | Pz | — | Ph | H | H | H | H | | | | | | formula 12 | | | |
| 565 | Rh | 1 | 2 | Pz | — | Ph | H | H | H | H | | | | | | formula 13 | | | |
| 566 | Rh | 1 | 2 | Pz | — | Ph | H | H | H | H | | | | | | formula 14 | | | |
| 567 | Rh | 1 | 2 | Pa | — | Ph | H | H | — | H | | | | | | formula 11 | | | |
| 568 | Rh | 1 | 2 | Pa | — | Ph | H | H | — | H | | | | | | formula 12 | | | |
| 569 | Rh | 1 | 2 | Pa | — | Ph | H | H | — | H | | | | | | formula 13 | | | |
| 570 | Rh | 1 | 2 | Pa | — | Ph | H | H | — | H | | | | | | formula 14 | | | |
| 571 | Pt | 1 | 1 | Pr | — | Ph | H | H | H | H | Pr | Tn1 | H | H | H | H | | | |
| 572 | Pt | 1 | 1 | Pr | — | Ph | H | H | H | H | Pr | Tn2 | H | H | H | H | | | |
| 573 | Pt | 1 | 1 | Pr | — | Ph | H | H | H | H | Pr | Tn3 | H | H | H | H | | | |
| 574 | Pt | 1 | 1 | Pr | — | Ph | H | H | H | H | Pr | Np | H | H | H | H | | | |
| 575 | Pt | 1 | 1 | Pr | — | Ph | H | H | H | H | Pr | Qn1 | H | H | H | H | | | |
| 576 | Pt | 1 | 1 | Pr | — | Ph | H | H | H | H | Pr | Qn2 | H | H | H | H | | | |
| 577 | Pt | 1 | 1 | Pr | — | Ph | H | H | H | H | Pr | Qx | H | H | H | H | | | |
| 578 | Pt | 1 | 1 | Pr | — | Ph | H | H | H | H | Pr | Qz1 | — | H | H | H | | | |
| 579 | Pt | 1 | 1 | Pr | — | Ph | H | H | H | H | Pr | Qz2 | H | — | H | H | | | |
| 580 | Pt | 1 | 1 | Pr | — | Ph | H | H | H | H | Pr | Cn1 | — | H | H | H | | | |
| 581 | Pt | 1 | 1 | Pr | — | Ph | H | H | H | H | Pr | Cn2 | H | — | H | H | | | |
| 582 | Pt | 1 | 1 | Pr | — | Ph | H | H | H | H | Pr | Pz | — | — | H | H | | | |
| 583 | Pt | 1 | 1 | Pr | — | Ph | H | H | H | H | Pr | Ph | CH3 | H | H | H | | | |
| 584 | Pt | 1 | 1 | Pr | — | Ph | H | H | H | H | Pr | Ph | H | CF3 | H | H | | | |
| 585 | Pt | 1 | 1 | Pr | — | Ph | H | H | H | H | Pr | tn3 | H | H | H | CF3 | | | |
| 586 | Pt | 1 | 1 | Pr | — | Tn1 | H | H | H | H | Pr | Tn3 | H | H | H | H | | | |
| 587 | Pt | 1 | 1 | Pr | — | Tn1 | H | H | H | H | Pr | Np | H | H | H | H | | | |
| 588 | Pt | 1 | 1 | Pr | — | Tn1 | H | H | H | H | Pr | Qn1 | H | H | H | H | | | |
| 589 | Pt | 1 | 1 | Pr | — | Tn1 | H | H | H | H | Pr | Qn2 | H | H | H | H | | | |
| 590 | Pt | 1 | 1 | Pr | — | Tn1 | H | H | H | H | Pr | Qx | H | H | H | H | | | |
| 591 | Pt | 1 | 1 | Pr | — | Tn1 | H | H | H | H | Pr | Qz1 | — | H | H | H | | | |
| 592 | Pt | 1 | 1 | Pr | — | Tn1 | H | H | H | H | Pr | Qz2 | H | — | H | H | | | |
| 593 | Pt | 1 | 1 | Pr | — | Tn1 | H | H | H | H | Pr | Cn1 | — | H | H | H | | | |

TABLE 1-continued

| | | | | | | | | | | | | | | | | | |
|---|---|---|---|---|---|---|---|---|---|---|---|---|---|---|---|---|---|
| 594 | Pt | 1 | 1 | Pr | — | Tn1 | H | H | H | H | Pr | Cn2 | H | — | H | H | |
| 595 | Pt | 1 | 1 | Pr | — | Tn1 | H | H | H | H | Pr | Pz | — | — | H | H | |
| 596 | Pt | 1 | 1 | Pr | — | Tn1 | H | H | H | H | Pr | Ph | CH3 | H | H | H | |
| 597 | Pt | 1 | 1 | Pr | — | Tn1 | H | H | H | H | Pr | Ph | H | CF3 | H | H | |
| 598 | Pt | 1 | 1 | Pr | — | Tn1 | H | H | H | H | Pr | tn3 | H | H | H | CF3 | |
| 599 | Pt | 1 | 1 | Pr | — | Ph | H | H | H | H | | | | | | | formula 11 |
| 600 | Pt | 1 | 1 | Pr | — | Ph | H | H | H | H | | | | | | | formula 12 |
| 601 | Pt | 1 | 1 | Pr | — | Ph | H | H | H | H | | | | | | | formula 13 |
| 602 | Pt | 1 | 1 | Pr | — | Ph | H | H | H | H | | | | | | | formula 14 |
| 603 | Pt | 1 | 1 | Pr | — | Tn1 | H | H | H | H | | | | | | | formula 11 |
| 604 | Pt | 1 | 1 | Pr | — | Tn1 | H | H | H | H | | | | | | | formula 12 |
| 605 | Pt | 1 | 1 | Pr | — | Tn1 | H | H | H | H | | | | | | | formula 13 |
| 606 | Pt | 1 | 1 | Pr | — | Tn1 | H | H | H | H | | | | | | | formula 14 |
| 607 | Pt | 1 | 1 | Pr | — | Tn3 | H | H | H | H | | | | | | | formula 11 |
| 608 | Pt | 1 | 1 | Pr | — | Tn3 | H | H | H | H | | | | | | | formula 12 |
| 609 | Pt | 1 | 1 | Pr | — | Tn3 | H | H | H | H | | | | | | | formula 13 |
| 610 | Pt | 1 | 1 | Pr | — | Tn3 | H | H | H | H | | | | | | | formula 14 |
| 611 | Pt | 1 | 1 | Pr | — | Np | H | H | H | H | | | | | | | formula 11 |
| 612 | Pt | 1 | 1 | Pr | — | Np | H | H | H | H | | | | | | | formula 12 |
| 613 | Pt | 1 | 1 | Pr | — | Np | H | H | H | H | | | | | | | formula 13 |
| 614 | Pt | 1 | 1 | Pr | — | Np | H | H | H | H | | | | | | | formula 14 |
| 615 | Pt | 1 | 1 | Pr | — | Qn2 | H | H | H | H | | | | | | | formula 11 |
| 616 | Pt | 1 | 1 | Pr | — | Qn2 | H | H | H | H | | | | | | | formula 12 |
| 617 | Pt | 1 | 1 | Pr | — | Qn2 | H | H | H | H | | | | | | | formula 13 |
| 618 | Pt | 1 | 1 | Pr | — | Qn2 | H | H | H | H | | | | | | | formula 14 |
| 619 | Pt | 1 | 1 | Py1 | — | Ph | H | H | H | — | | | | | | | formula 11 |
| 620 | Pt | 1 | 1 | Py1 | — | Ph | H | H | H | — | | | | | | | formula 12 |
| 621 | Pt | 1 | 1 | Py1 | — | Ph | H | H | H | — | | | | | | | formula 13 |
| 622 | Pt | 1 | 1 | Py1 | — | Ph | H | H | H | — | | | | | | | formula 14 |
| 623 | Pt | 1 | 1 | Py2 | — | Ph | H | H | H | H | | | | | | | formula 11 |
| 624 | Pt | 1 | 1 | Py2 | — | Ph | H | H | H | H | | | | | | | formula 12 |
| 625 | Pt | 1 | 1 | Py2 | — | Ph | H | H | H | H | | | | | | | formula 13 |
| 626 | Pt | 1 | 1 | Py2 | — | Ph | H | H | H | H | | | | | | | formula 14 |
| 627 | Pt | 1 | 1 | Pz | — | Ph | H | H | H | H | | | | | | | formula 11 |
| 628 | Pt | 1 | 1 | Pz | — | Ph | H | H | H | H | | | | | | | formula 12 |
| 629 | Pt | 1 | 1 | Pz | — | Ph | H | H | H | H | | | | | | | formula 13 |
| 630 | Pt | 1 | 1 | Pz | — | Ph | H | H | H | H | | | | | | | formula 14 |
| 631 | Pt | 1 | 1 | Pa | — | Ph | H | H | H | — | | | | | | | formula 11 |
| 632 | Pt | 1 | 1 | Pa | — | Ph | H | H | H | — | | | | | | | formula 12 |
| 633 | Pt | 1 | 1 | Pa | — | Ph | H | H | H | — | | | | | | | formula 13 |
| 634 | Pt | 1 | 1 | Pa | — | Ph | H | H | H | — | | | | | | | formula 14 |
| 635 | Pd | 1 | 1 | Pr | — | Ph | H | H | H | H | Pr | Tn1 | H | H | H | H | |
| 636 | Pd | 1 | 1 | Pr | — | Ph | H | H | H | H | Pr | Tn2 | H | H | H | H | |
| 637 | Pd | 1 | 1 | Pr | — | Ph | H | H | H | H | Pr | Tn3 | H | H | H | H | |
| 638 | Pd | 1 | 1 | Pr | — | Ph | H | H | H | H | Pr | Np | H | H | H | H | |
| 639 | Pd | 1 | 1 | Pr | — | Ph | H | H | H | H | Pr | Qn1 | H | H | H | H | |
| 640 | Pd | 1 | 1 | Pr | — | Ph | H | H | H | H | Pr | Qn2 | H | H | H | H | |
| 641 | Pd | 1 | 1 | Pr | — | Ph | H | H | H | H | Pr | Qx | H | H | H | H | |
| 642 | Pd | 1 | 1 | Pr | — | Ph | H | H | H | H | Pr | Qz1 | — | H | H | H | |
| 643 | Pd | 1 | 1 | Pr | — | Ph | H | H | H | H | Pr | Oz2 | H | — | H | H | |
| 644 | Pd | 1 | 1 | Pr | — | Ph | H | H | H | H | Pr | Cn1 | — | H | H | H | |
| 645 | Pd | 1 | 1 | Pr | — | Ph | H | H | H | H | Pr | Cn2 | H | — | H | H | |
| 646 | Pd | 1 | 1 | Pr | — | Ph | H | H | H | H | Pr | Pz | — | — | H | H | |
| 647 | Pd | 1 | 1 | Pr | — | Ph | H | H | H | H | Pr | Ph | CH3 | H | H | H | |
| 648 | Pd | 1 | 1 | Pr | — | Ph | H | H | H | H | Pr | Ph | H | CF3 | H | H | |
| 649 | Pd | 1 | 1 | Pr | — | Ph | H | H | H | H | Pr | tn3 | H | H | H | CF3 | |
| 650 | Pd | 1 | 1 | Pr | — | Tn1 | H | H | H | H | Pr | Tn3 | H | H | H | H | |
| 651 | Pd | 1 | 1 | Pr | — | Tn1 | H | H | H | H | Pr | Np | H | H | H | H | |
| 652 | Pd | 1 | 1 | Pr | — | Tn1 | H | H | H | H | Pr | Qn1 | H | H | H | H | |
| 653 | Pd | 1 | 1 | Pr | — | Tn1 | H | H | H | H | Pr | Qn2 | H | H | H | H | |
| 654 | Pd | 1 | 1 | Pr | — | Tn1 | H | H | H | H | Pr | Qx | H | H | H | H | |
| 655 | Pd | 1 | 1 | Pr | — | Tn1 | H | H | H | H | Pr | Qz1 | — | H | H | H | |
| 656 | Pd | 1 | 1 | Pr | — | Tn1 | H | H | H | H | Pr | Qz2 | H | — | H | H | |
| 657 | Pd | 1 | 1 | Pr | — | Tn1 | H | H | H | H | Pr | Cn1 | — | H | H | H | |
| 658 | Pd | 1 | 1 | Pr | — | Tn1 | H | H | H | H | Pr | Cn2 | H | — | H | H | |
| 659 | Pd | 1 | 1 | Pr | — | Tn1 | H | H | H | H | Pr | Pz | — | — | H | H | |
| 660 | Pd | 1 | 1 | Pr | — | Tn1 | H | H | H | H | Pr | Ph | CH3 | H | H | H | |
| 661 | Pd | 1 | 1 | Pr | — | Tn1 | H | H | H | H | Pr | Ph | H | CF3 | H | H | |
| 662 | Pd | 1 | 1 | Pr | — | Tn1 | H | H | H | H | Pr | tn3 | H | H | H | CF3 | |
| 663 | Pd | 1 | 1 | Pr | — | Ph | H | H | H | H | | | | | | | formula 11 |
| 664 | Pd | 1 | 1 | Pr | — | Ph | H | H | H | H | | | | | | | formula 12 |
| 665 | Pd | 1 | 1 | Pr | — | Ph | H | H | H | H | | | | | | | formula 13 |
| 666 | Pd | 1 | 1 | Pr | — | Ph | H | H | H | H | | | | | | | formula 14 |
| 667 | Pd | 1 | 1 | Pr | — | Tn1 | H | H | H | H | | | | | | | formula 11 |
| 668 | Pd | 1 | 1 | Pr | — | Tn1 | H | H | H | H | | | | | | | formula 12 |
| 669 | Pd | 1 | 1 | Pr | — | Tn1 | H | H | H | H | | | | | | | formula 13 |
| 670 | Pd | 1 | 1 | Pr | — | Tn1 | H | H | H | H | | | | | | | formula 14 |
| 671 | Pd | 1 | 1 | Pr | — | Tn3 | H | H | H | H | | | | | | | formula 11 |
| 672 | Pd | 1 | 1 | Pr | — | Tn3 | H | H | H | H | | | | | | | formula 12 |

TABLE 1-continued

| No | M | m | n | CyN1 | X/L | CyC1 | R1 | R2 | R3 | R4 | L' |
|---|---|---|---|---|---|---|---|---|---|---|---|
| 673 | Pd | 1 | 1 | Pr | — | Tn3 | H | H | H | H | formula 13 |
| 674 | Pd | 1 | 1 | Pr | — | Tn3 | H | H | H | H | formula 14 |
| 675 | Pd | 1 | 1 | Pr | — | Np | H | H | H | H | formula 11 |
| 676 | Pd | 1 | 1 | Pr | — | Np | H | H | H | H | formula 12 |
| 677 | Pd | 1 | 1 | Pr | — | Np | H | H | H | H | formula 13 |
| 678 | Pd | 1 | 1 | Pr | — | Np | H | H | H | H | formula 14 |
| 679 | Pd | 1 | 1 | Pr | — | Qn2 | H | H | H | H | formula 11 |
| 680 | Pd | 1 | 1 | Pr | — | Qn2 | H | H | H | H | formula 12 |
| 681 | Pd | 1 | 1 | Pr | — | Qn2 | H | H | H | H | formula 13 |
| 682 | Pd | 1 | 1 | Pr | — | Qn2 | H | H | H | H | formula 14 |
| 683 | Pd | 1 | 1 | Py1 | — | Ph | H | H | H | — | formula 11 |
| 684 | Pd | 1 | 1 | Py1 | — | Ph | H | H | H | — | formula 12 |
| 685 | Pd | 1 | 1 | Py1 | — | Ph | H | H | H | — | formula 13 |
| 686 | Pd | 1 | 1 | Py1 | — | Ph | H | H | H | — | formula 14 |
| 687 | Pd | 1 | 1 | Py2 | — | Ph | H | H | H | H | formula 11 |
| 688 | Pd | 1 | 1 | Py2 | — | Ph | H | H | H | H | formula 12 |
| 689 | Pd | 1 | 1 | Py2 | — | Ph | H | H | H | H | formula 13 |
| 690 | Pd | 1 | 1 | Py2 | — | Ph | H | H | H | H | formula 14 |
| 691 | Pd | 1 | 1 | Pz | — | Ph | H | H | H | H | formula 11 |
| 692 | Pd | 1 | 1 | Pz | — | Ph | H | H | H | H | formula 12 |
| 693 | Pd | 1 | 1 | Pz | — | Ph | H | H | H | H | formula 13 |
| 694 | Pd | 1 | 1 | Pz | — | Ph | H | H | H | H | formula 14 |
| 695 | Pd | 1 | 1 | Pa | — | Ph | H | H | — | H | formula 11 |
| 696 | Pd | 1 | 1 | Pa | — | Ph | H | H | — | H | formula 12 |
| 697 | Pd | 1 | 1 | Pa | — | Ph | H | H | — | H | formula 13 |
| 698 | Pd | 1 | 1 | Pa | — | Ph | H | H | — | H | formula 14 |

| No | M | m | n | CyN1 | L\\X/ | CyC1 | R1 | R2 | R3 | R4 | R5 | R6 | L' |
|---|---|---|---|---|---|---|---|---|---|---|---|---|---|
| 699 | Ir | 2 | 0 | Pr | CR2 | Ph | H | H | H | H | F | F | CH3—CO—CH—CO—CH3 |
| 700 | Ir | 3 | 0 | Pr | CR2 | Ph | H | H | H | H | F | F | |

Hereinbelow, the present invention will be described more specifically based on Examples with reference to the drawing.

EXAMPLES 1 AND 2

In these examples, the following metal coordination compounds of formula (1) (Ex. Comp. Nos. 37 and 1) were used in respective luminescence layers for Examples 1 and 2 respectively.

Ex. Comp. No. 37

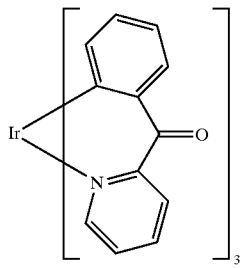

Ex. Comp. No. 1

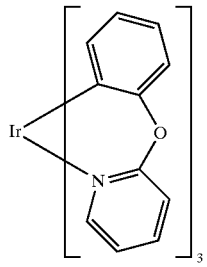

Each of organic luminescence devices having a structure including four organic (compound) layers (luminescence function layers) shown in FIG. 1C were prepared in the following manner.

On a 1.1 mm-thick glass substrate (transparent substrate 15), a 100 nm-thick film (transparent electrode 14) of ITO (indium tin oxide) was formed by sputtering, followed by patterning to have an (opposing) electrode area of 3 mm$^2$.

On the ITO-formed substrate, four organic layers and two metal electrode layers shown below were successively formed by vacuum (vapor) deposition using resistance heating in a vacuum chamber ($10^{-4}$ Pa).

Organic layer 1 (hole transport layer 13) (50 nm): α-NPD

Organic layer 2 (luminescence layer 12) (40 nm): CBP: metal coordination compound of formula (1) (93:7 by weight) (co-vacuum deposition)

Organic layer 3 (exciton diffusion prevention layer 17) (20 nm): BCP

Organic layer 4 (electron transport layer 16) (40 nm): Alq3

Metal electrode layer 1 (metal electrode 11) (15 nm): Al—Li alloy (Li=1.8 wt. %)

Metal electrode layer 2 (metal electrode 11) (100 nm): Al

EL characteristics of the luminescence devices using the metal coordination compounds of formula (1) (Ex. Comp. Nos. 37 and 1) were measured by using a microammeter ("Model 4140B", mfd. by Hewlett-Packard Co.) for a current density under application of a voltage of 20 volts using a luminance meter ("Model BM7", mfd. by Topcon K.K.) for a luminescence efficiency (luminescence luminance). Further, both the above-prepared luminescence devices showed a good rectification characteristic.

The results are shown below.

| Ex. No. | Ex. Comp. No. | Luminance (cd/m$^2$) |
|---------|---------------|----------------------|
| 1       | 37            | 50                   |
| 2       | 1             | 25                   |

Each of luminescence states of the organic luminescence devices was similar to that based on photoluminescence (luminescence center wavelength) in the case where each of the luminescence materials (Ex. Comp. Nos. 37 and Ex. Comp. No. 1 as luminescence sources in these examples) was dissolved in toluene.

Accordingly, luminescence from these organic luminescence devices was found to be resulting from the corresponding luminescence material.

EXAMPLE 3

Figure 2:
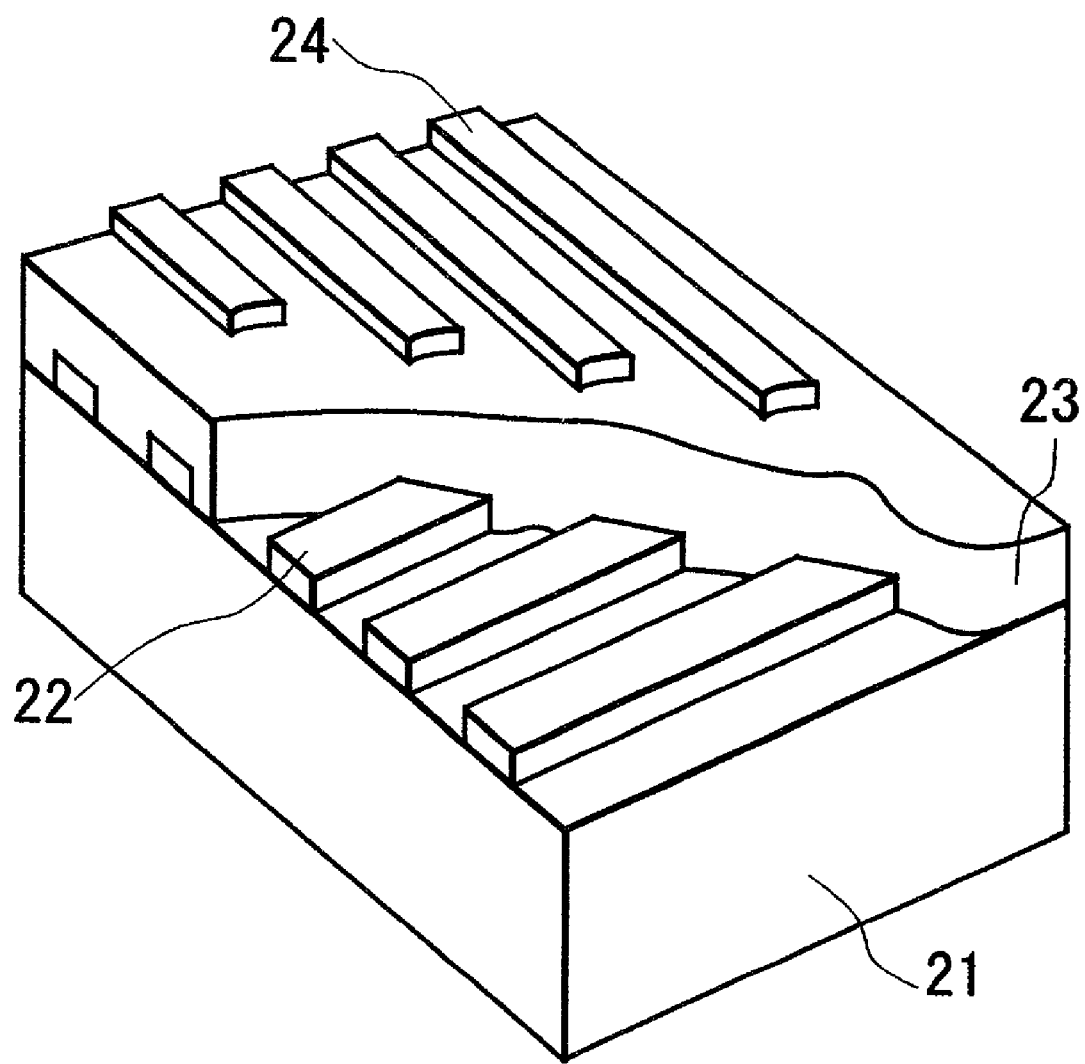
FIG. 2 is a schematic perspective view of an organic luminescence device of a single matrix-type used in Example 3 appearing hereinafter.

A simple matrix-type organic EL device shown in FIG. 2 was prepared in the following manner.

On a 1.1 mm-thick glass substrate 21 (75×75 mm), a ca. 100 nm-thick transparent electrode 22 of ITO (as an anode) was formed by sputtering, followed by patterning in a stripe form comprising 100 lines (each having a width of 100 μm and a spacing of 40 μm).

On the ITO electrode 22, an organic lamination layer 23 including four organic layers was formed in the same manner as in Example 1.

Then, on the organic lamination layer 23, a metal electrode comprising a 10 nm-thick Al—Li alloy layer (Li: 1.3 wt. %) and a 150 nm-thick Al layer (disposed on the Al—Li alloy layer) was formed by vacuum deposition (2.7×10$^{-3}$ Pa (=2×10$^{-5}$ Torr)) with a mask, followed by patterning in a stripe form comprising 100 lines (each having a width of 100 μm and a spacing of 40 μm) arranged to intersect the ITO stripe electrode lines at right angles, thus forming an organic EL device having a matrix of pixels (100×100 pixels).

Figure 3:
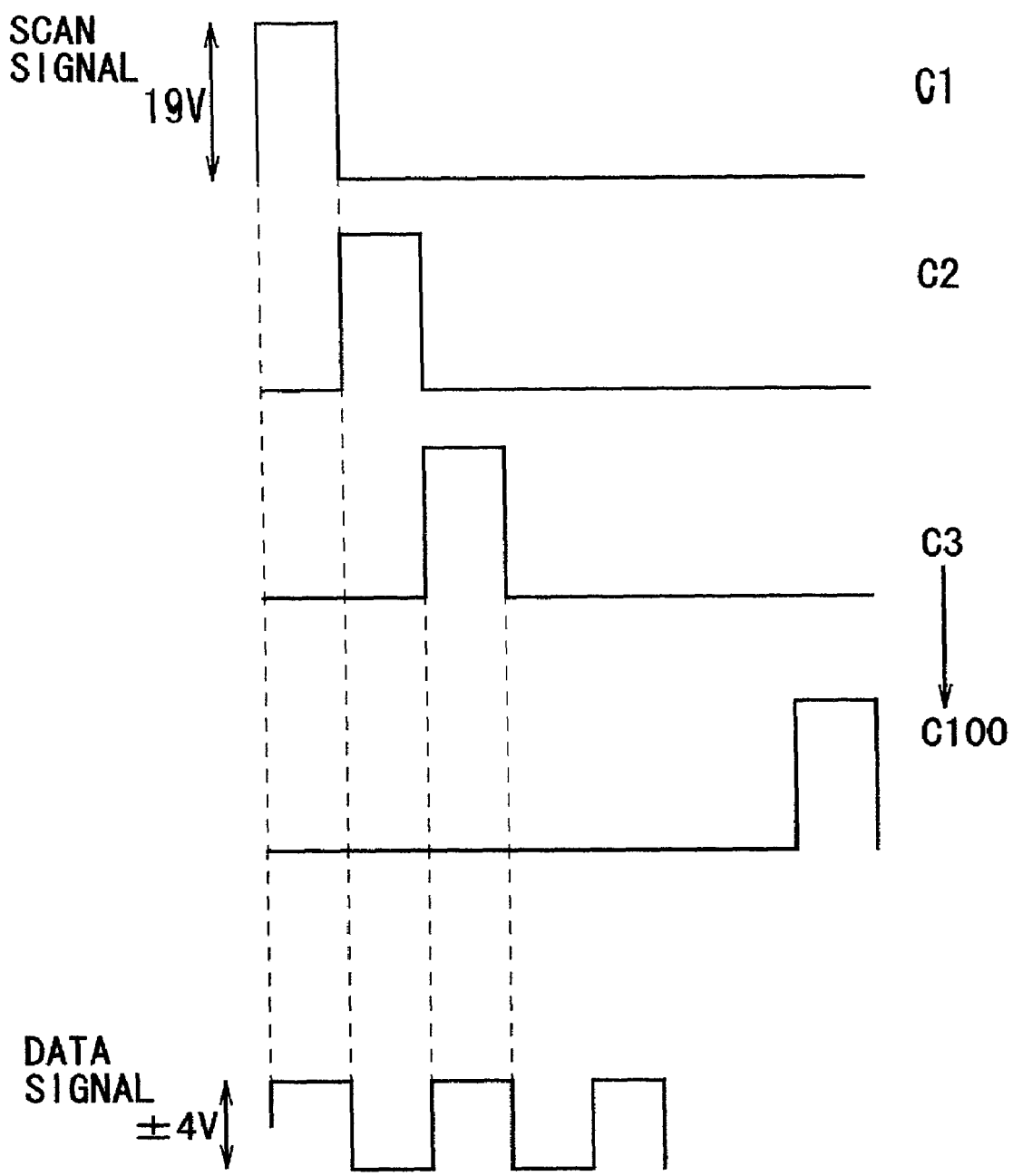
FIG. 3 is a waveform diagram of a driving signal employed in Example 3.

The thus-prepared organic EL device was placed in a glove box and driven in a simple matrix manner (frame frequency: 30 Hz, interlace scanning) by applying a driving waveform (drive voltage: 15 to 23 volts, scanning signal voltage: 19 volts, data signal voltage: ±4 volts) as shown in FIG. 3.

As a result, a smooth motion picture display by the organic EL device was confirmed.

EXAMPLE 4

An organic EL device was prepared in the same manner as in Example 1 except that the metal coordination compound (Ex. Comp. No. 37) was changed to a metal coordination compound of the formula 41 (specifically shown hereinabove).

When the EL device was supplied with a voltage of 20 volts, stable and high-efficiency yellowish green luminescence resulting from the thienylpyridine ligand of the metal coordination compound of the formula 41 was confirmed. The luminescence was stable even when the EL device was continuously driven for 100 hours.

EXAMPLE 5

An organic EL device was prepared in the same manner as in Example 1 except that the metal coordination compound (Ex. Comp. No. 37) was changed to a metal coordination compound of the formula 44 (specifically shown hereinabove).

When the EL device was supplied with a voltage of 20 volts, stable and high-efficiency reddish orange luminescence resulting from the metal coordination compound of the formula 44 was confirmed. The luminescence was stable even when the EL device was continuously driven for 100 hours.

EXAMPLE 6

An organic EL device was prepared in the same manner as in Example 1 except that the metal coordination compound (Ex. Comp. No. 37) was changed to a metal coordination compound of the formula 46 (specifically shown hereinabove).

When the EL device was supplied with a voltage of 20 volts, stable and high-efficiency reddish orange luminescence resulting from the metal coordination compound of the formula 46 was confirmed. The luminescence was stable even when the EL device was continuously driven for 100 hours.

EXAMPLE 7

An organic EL device was prepared in the same manner as in Example 1 except that the metal coordination compound (Ex. Comp. No. 37) was changed to a metal coordination compound of the formula 49 (specifically shown hereinabove).

When the EL device was supplied with a voltage of 20 volts, stable and high-efficiency reddish orange luminescence resulting from the metal coordination compound of the formula 49 was confirmed. The luminescence was stable even when the EL device was continuously driven for 100 hours.

EXAMPLE 8

An organic EL device was prepared in the same manner as in Example 1 except that the metal coordination compound (Ex. Comp. No. 37) was changed to a metal coordination compound of the formula 50 (specifically shown hereinabove).

When the EL device was supplied with a voltage of 20 volts, stable and high-efficiency reddish orange luminescence resulting from the metal coordination compound of the formula 50 was confirmed. The luminescence was stable even when the EL device was continuously driven for 100 hours.

EXAMPLE 9

An organic EL device was prepared in the same manner as in Example 1 except that the metal coordination compound (Ex. Comp. No. 37) was changed to a metal coordination compound of the formula 42 (specifically shown hereinabove).

When the EL device was supplied with a voltage of 20 volts, stable and high-efficiency green luminescence resulting from the metal coordination compound of the formula 42 was confirmed. The luminescence was stable even when the EL device was continuously driven for 100 hours.

In the above Examples 4–9, all the metal coordination compounds according to the present invention improved a luminescence efficiency by ca. 20% when compared with corresponding metal coordination compounds having a single luminescent ligand structure, respectively.

EXAMPLE 10

Ir-based metal coordination compounds of the formula (1) according to the present invention were basically synthesized through the following reaction schemes.

$$Ir(CH_3COCHCOCH_3)_3 = Ir(acac)_3 \xrightarrow{3XL} Ir(L)_3$$

or $$IrCl_3 \cdot xH_2O \xrightarrow{L} [IrL_2Cl_2] \xrightarrow{L} 2IrL_3$$

In the above, as a starting material, a commercially available Ir acetylacetonato complex or a commercially available hydrated Ir chloride was used. "L" denotes a ligand of an objective Ir complex.

In a specific synthesis example, a metal coordination compound (Ex. Comp. No. 49) was prepared in the following manner.

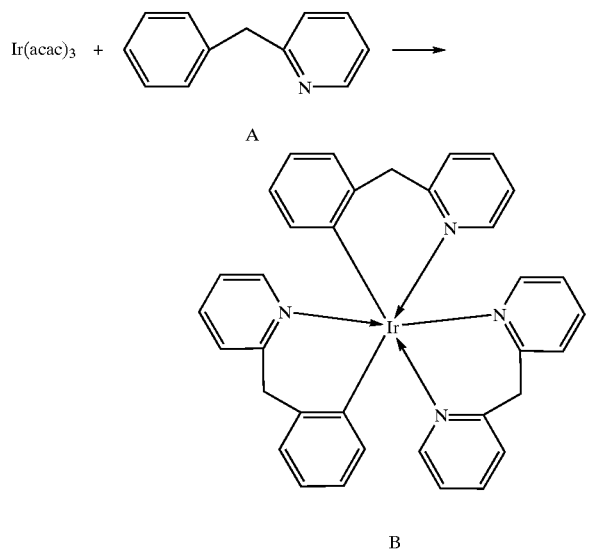

In a 100-four-necked flask, 50 ml of glycerol was placed and stirred for 2 hours at 130–140° C. while supplying nitrogen gas into glycerol, followed by cooling by standing to 100° C. At that temperature, 1.02 g (5.0 mM) of 2-benzylpyridine of formula A and 0.5 g (1.0 mM) of Ir(III) acetyl-acetonate (Ir(acac)$_3$) were added to the system, followed by stirring for 7 hours at ca. 210° C. in a nitrogen gas stream atmosphere.

The reaction mixture was cooled to room temperature and poured into 300 ml of 1N-hydrochloric acid. The resultant precipitate was recovered by filtration and washed with water, followed by purification by silica gel column chromatography (eluent: chloroform) to obtain 0.11 g of a black solid metal coordination compound (Ex. Comp. No. 49 of formula B) (Yield: 16%).

The thus-prepared metal coordination compound was subjected to MALDI-TOF-MS (Matrix-assisted Laser Desorption Ionization mass spectroscopy), whereby M$^+$ (mass number of ionized objective product) of 697.2 (as a molecular weight) was confirmed.

Figure 5:
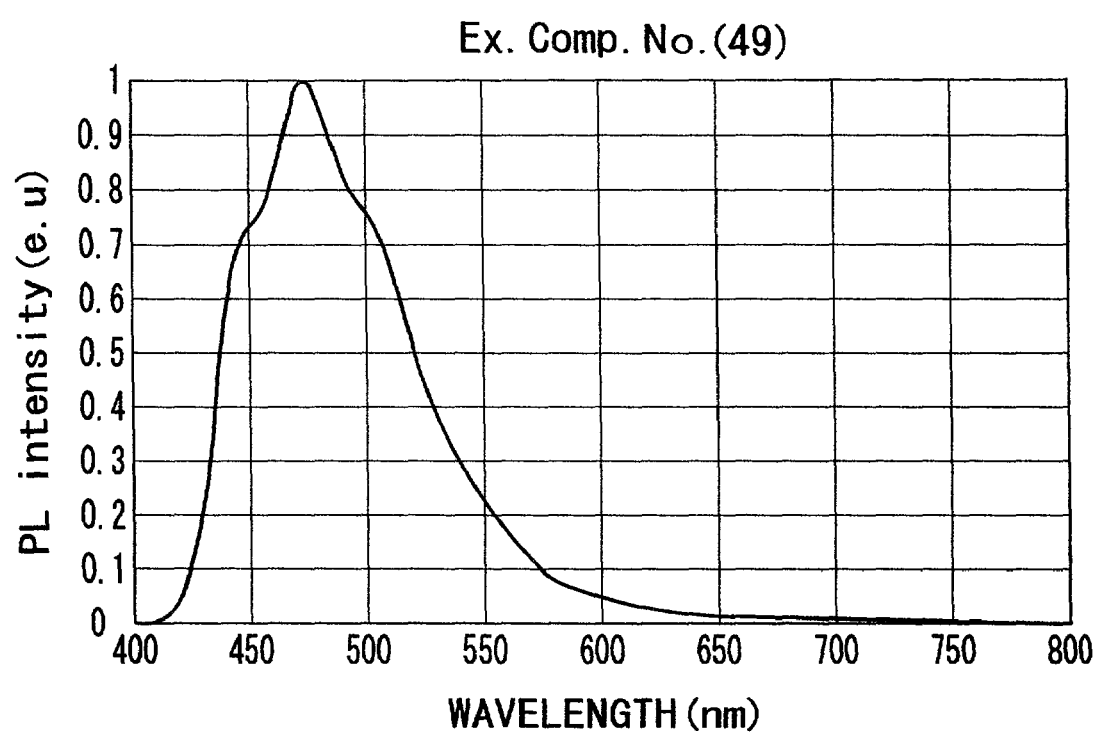
FIG. 5 shows a luminescence spectrum diagram of 2-benzylpyridine Ir complex used in Example 10.

When the metal coordination compound was dissolved in toluene and subjected to measurement of luminescence spectrum, the metal coordination compound provided a luminescence spectrum diagram including a maximum luminescence wavelength λmax of 463 nm as shown in FIG. 5.

Further, when Ir(ppy)$_3$ described hereinabove was used as a standard compound exhibiting a phosphorescence yield φ (Ir(ppy)$_3$) of 1, the metal coordination compound (Ex. Comp. No. 49) exhibited a phosphorescence yield φ (unknown) of 0.6.

Herein, the phosphorescence yield φ (φ (unknown)) may be obtained according to the following equation:

$$\phi \text{ (unknown)}/\phi \text{ }(Ir(ppy)_3) =$$

$$[Sem \text{ (unknown)}/Iabs \text{ (unknown)}]/[Sem \text{ }(Ir(ppy)_3)/Iabs \text{ }(Ir(ppy)_3)],$$

wherein φ (unknown) represents a phosphorescence yield of an unknown (objective) compound, φ (Ir(ppy)$_3$) represents a phosphorescence yield of Ir(ppy)$_3$ (=1 in this case) Sem (unknown) represents an absorption coefficient of an unknown compound at its excitation wavelength, Iabs (unknown) represents an areal intensity of emission spectrum of the unknown compound excited at the excitation wavelength, Sem (Ir(ppy)$_3$ represents an absorption coefficient of Ir(ppy)$_3$ at its excitation wavelength, and Iabs (Ir(ppy)$_3$) represents an areal intensity of emission spectrum of Ir(ppy)$_3$ excited at the excitation wavelength.

EXAMPLE 11

In this example, the metal coordination compound (Ex. Comp. No. 49) prepared in Example 10 was mixed with polyvinyl carbazole (PVK) shown below in a weight ratio of 8:92 to obtain a luminescent material used for a luminescence layer.

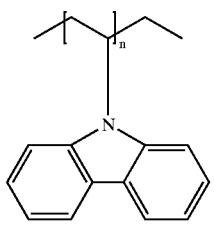

An organic EL device was prepared in the following manner.

A 1.1 mm-thick glass substrate provided with a 70 nm-thick ITO electrode (as an anode electrode) was subjected to plasma-ozone washing.

On the thus-treated glass substrate, a solution of the above-prepared luminescent material (mixture of the metal coordination compound (Ex. Comp. No. 49) and PVK) in chloroform was spin-coated at 2000 ppm, followed by drying to obtain a luminescence layer having a thickness of 90±10 nm.

The thus-treated glass substrate was then placed in a vacuum deposition chamber. On the luminescence layer of the substrate, a 30 nm-thick Mg—Ag alloy layer and a 100 nm-thick Al layer (as a cathode electrode) were successively formed by vacuum deposition (at most $10^{-4}$ Pa), thus preparing an organic EL device.

When a DC voltage of 8–12 volts was applied between the ITO electrode (anode) and the metal electrode (cathode), clear blue luminescence was confirmed.

Further, the luminescence material (mixture) after drying exhibited a maximum luminescence wavelength was 490 nm closer to that (473 nm) of the metal coordination compound (Ex. Comp. No. 49) in toluene solution used in Example 10. Accordingly, the luminescence in this example was resulting from the metal coordination compound (Ex. Comp. No. 49).

After the DC voltage application, an attenuation time for the blue luminescence was at least 0.3–0.5 sec. As a result, the blue luminescence in this example was supported to be phosphorescence attributable to the metal coordination compound (Ex. Comp. No. 49).

The blue luminescence state was stable even when the EL device was continuously driven for 12 hours.

EXAMPLES 12 AND 13

In these examples, metal coordination compound (of formulas 43 and 51 specifically shown above) were synthesized through the following steps 1) to 4).

Step 1) (Synthesis of 2-(pyridine-2-yl)benzo[b]-thiophene

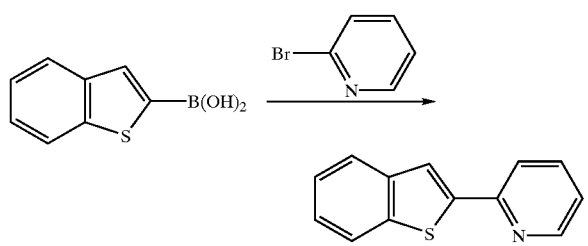

In a 1 liter-three-necked flask, 26.6 g (168.5 mM) of 2-bromopyridine, 30.0 g (168.5 mM) of benzo[b]thiophene-2-boric acid, 170 ml of toluene, 85 ml of ethanol and 170 ml of 2M-sodium carbonate aqueous solution were placed, and to the mixture, under stirring in a nitrogen gas stream atmosphere, 6.18 g (5.35 mM)of tetrakis-(triphenylphosphin) palladium (O) was added, followed by refluxing under stirring for 5.5 hours in a nitrogen gas stream atmosphere.

After the reaction, the reaction mixture was cooled and subjected to extraction with cold water and toluene.

The organic layer was washed with water until the layer became neutral, followed by distilling-off of the solvent under reduced pressure to obtain a residue. The residue was purified by silica gel column chromatography (eluent: toluene/hexane=5/1) and then by alumina column chromatography (eluent: toluene) and was recrystallized from ethanol to obtain 12.6 g o 2-(pyridine-2-yl)benzo[b]thiophene (Yield: 35.4%).

Step 2) (Synthesis of tetrakis(2-benzo[b]-thiophene-2-yl)pyridine-$C^3$,N)($\mu$-dichloro)diiridium (III)

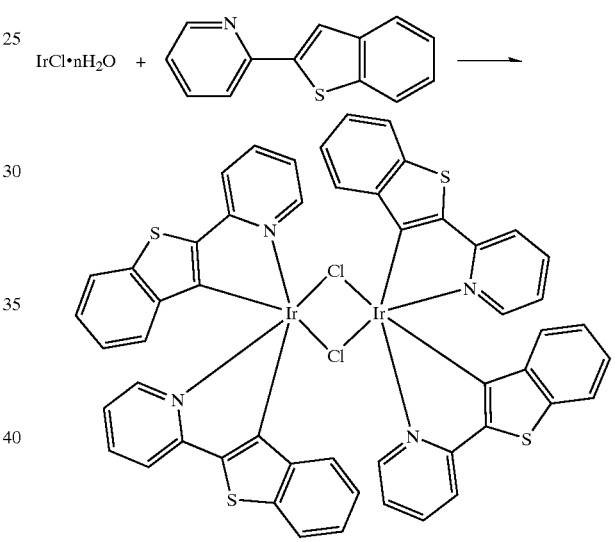

In a 500 ml-three-necked flask, 3.65 g (10.4 mM) of n-hydrated iridium (III) chloride (IrCl·nH$_2$O), 4.82 g (22.8 mM) of 2-(benzo[b]thiophene-2-yl)pyridine, 150 ml of 2-ethoxy ethanol and 50 ml of water were placed and stirred for 0.5 hour at room temperature in an argon gas atmosphere. The mixture was then gradually heated and subjected to refluxing for ca. 24 hours under stirring.

After cooling, the reaction mixture was subjected to filtration, followed by washing with ethanol and acetone.

The resultant powder was dissolved in chloroform and subjected to extraction with water. The organic layer was dried with anhydrous magnesium sulfate, followed distilling-off of the solvent to obtain a residue. The residue was recrystallized from a mixture solvent (hexanemethylene chloride) to obtain 5.40 g of tetrakis(2-(benzo[b]thiophene-2-yl)pyridine-$C^3$, N) ($\mu$-dichloro)diiridium (III) (Yield: 80.1%).

Step 3) Synthesis of bis(2-(benzo[b]thiophene-2-yl)pyridine-$C^3$,N) (acetylacetonato)iridium (III)

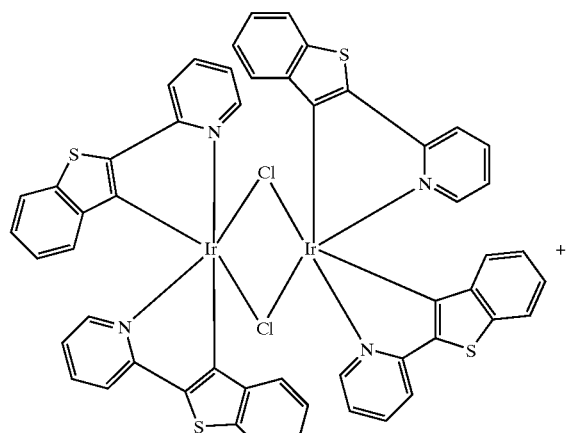

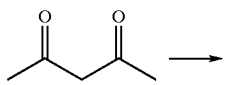

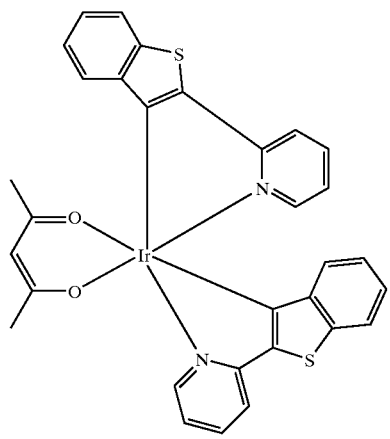

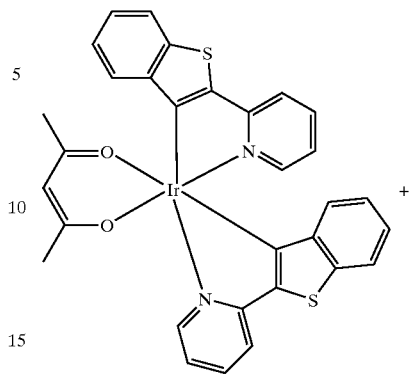

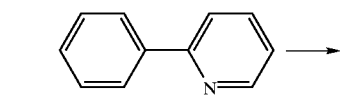

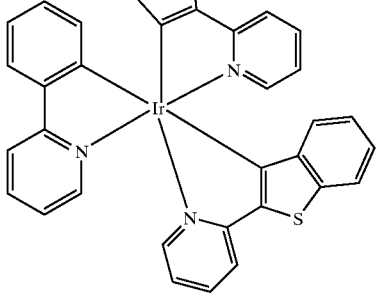

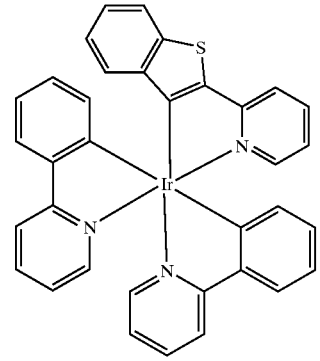

In a 500 ml-three-necked flask, 2.2 g (1.70 mM) of tetrakis (2-(benzo[b]thiophene-2-yl) pyridine-$C^3$,N) ($\mu$-dichloro)diiridium, 0.51 g (5.09 mM) of acetylacetone, 2.5 g of sodium carbonate and 150 ml of ethanol were placed and stirred for 1 hour in an argon gas stream atmosphere.

The mixture was then gradually heated and subjected to refluxing for 15 hours under stirring.

After the reaction, the reaction mixture was cooled. The resultant precipitate was recovered by filtration and washed with water and ethanol to obtain a residue. The residue was purified by silica gel column chromatography (eluent: chloroform) and recrystallized from ethanol to obtain 1.87 g of bis(2-(benzo[b]thiophene-2-yl)pyridine-$C^3$,N) (acetylacetonato)iridium (III) (Yield: 77.3%).

Step 4) (Synthesis of bis(2-(benzo[b]thiophene-2-yl)pyridine-$C^3$,N) (phenylpyridine-$C^2$,N) iridium (III) (metal coordination compound of formula 51) and bis(phenylpyridine-$C^2$,N) (2-(benzo[b]thiophene-2-yl)pyridine-$C^3$,N) iridium (III) (metal coordination compound of formula 43))

In a 100 ml-three-necked flask, 50 ml of glycerol was placed and air in the interior of the flask was aerated with argon gas. Under stirring, 0.7 g (1.00 mM) of bis(2-benzo[b]thiophene-2-yl) pyridine-$C^3$,N) (acetylacetonato)iridium (III) and 0.39 g (2.50 mM) of 2-phenylpyridine were added to the glycerol, followed by stirring for 10 hours at 200° C.

After the reaction, to the reaction mixture, 300 ml of 1N-hydrochloric acid was added, followed by filtration. The resultant residue was purified by silica gel column chromatography (eluent: chloroform) and then fractionation by high-performance liquid chromatography to obtain 108 mg of bis(2-(benzo[b]thiophene-2-yl)pyridine-$C^3$,N) (phenylpyridine-$C^2$,N)iridium (III) (metal coordination compound of formula 51) and 35 mg of bis(phenylpyridine-$C^2$, N) (2-(benzo[b]thiophene-2-yl)pyridine-$C^3$,N) iridium (III) (metal coordination compound of formula 43)).

The thus-prepared metal coordination compounds (of formulas 51 and 43) were subjected to MALDI-TOF-MS, respectively, whereby M+ of 767.1 for the metal coordination compound of formula 51 and M+ of 711.1 for the metal coordination compound of formula 43 were confirmed, respectively.

When each of the metal coordination compounds of formulas 51 and 43 was dissolved in toluene and are subjected to measurement of luminescence spectrum, both the metal coordination compounds of formulas 51 and 43 exhibited a maximum luminescence wavelength λmax of 598 nm, thus confirming that the luminescence was attributable to the benzothienyl ligand.

Further, when Ir(ppy)$_3$ described hereinabove was used as a standard compound exhibiting a phosphorescence yield φ of 1, the metal coordination compound of formula 51 exhibited a phosphorescence yield φ of 0.2 and the metal coordination compound of formula 43 exhibited a phosphorescence yield φ of 0.3.

In order to confirm that the luminescence was phosphorescence, each of the metal coordination compounds of formulas 51 and 43 was dissolved in chloroform to prepare a first solution and a second solution. Each first solution was subjected to aeration with oxygen gas and each second solution was subjected to aeration with nitrogen gas.

When each of the thus-prepared first and second solutions were subjected to light irradiation, the oxygen-aerated solution exhibited substantially no phosphorescence but the nitrogen-aerated solution exhibited phosphorescence. As a result, these metal coordination compounds of formulas 51 and 43 were found to be phosphorescent metal coordination compounds.

The metal coordination compounds of formulas 51 and 43 were then subjected to measurement of luminescence life (time) in the following manner.

Each of the metal coordination compounds of formulas 51 and 43 was dissolved in chloroform and was spin-coated on a quartz substrate to form a ca. 0.1 μm-thick metal coordination compound layer.

By using a luminescence life-measuring apparatus (available from Hamamatsu Photonics K.K.), the above-prepared metal coordination compound layer formed on the substrate was subjected to pulse irradiation with nitrogen laser light (excitation wavelength: 337 nm) at room temperature to measure an attenuation time immediately after the excitation laser pulse irradiation.

A luminescence intensity I after a lapse of t (sec) is defined as the following equation:

$$I = I_0 \exp(-t/\tau),$$

wherein $I_0$ represents an initial luminescence intensity and τ (μsec) represents a luminescence life (time).

As a result, both the metal coordination compounds of formulas 51 and 43 showed a shorter luminescence life of at most 10 μsec.

Accordingly, the metal coordination compound of the present invention is expected to provide an organic EL device using the metal coordination compound with a good stability since the metal coordination compound exhibits phosphorescent luminescence and a shorter phosphorescence life (time).

EXAMPLES 14 AND 15

Two organic EL devices using the metal coordination compound of formulas 51 and 43 prepared in Examples 12 and 13 were prepared in these examples.

Each of the organic luminescence devices had a structure including four organic (compound) layers (luminescence function layers) shown in FIG. 1C and was prepared in the following manner.

On a 1.1 mm-thick glass substrate (transparent substrate 15), a 100 nm-thick film (transparent electrode 14) of ITO (indium tin oxide) was formed by sputtering, followed by patterning to have an (opposing) electrode area of 3 mm².

On the ITO-formed substrate, four organic layers and two metal electrode layers shown below were successively formed by vacuum (vapor) deposition using resistance heating in a vacuum chamber (10$^{-4}$ Pa).

Organic layer 1 (hole transport layer 13) (50 nm): α-NPD

Organic layer 2 (luminescence layer 12) (40 nm): CBP: metal coordination compound of formula (1) (93:7 by weight) (co-vacuum deposition)

Organic layer 3 (exciton diffusion prevention layer 17) (20 nm): BCP

Organic layer 4 (electron transport layer 16) (40 nm): Alq3

Metal electrode layer 1 (metal electrode 11) (15 nm): Al—Li alloy (Li=1.8 wt. %)

Metal electrode layer 2 (metal electrode 11) (100 nm): Al

EL characteristics of the luminescence devices using the metal coordination compounds of formulas 51 and 43 were measured by using a microammeter ("Model 4140B", mfd. by Hewlett-Packard Co.) for a current density under application of a voltage of 8 volts (current-voltage characteristic), using a spectrophotofluoro-meter ("Model SR1", mfd. by Topcon K.K.) for a maximum luminescence wavelength λmax, and using a luminance meter ("Model BM7", mfd. by Topcon K.K.) for a luminescence efficiency. Further, both the above-prepared luminescence devices showed a good rectification characteristic.

The results are shown below.

| Ex. No. | Formula | λmax (nm) | Luminance (cd/m²) |
| --- | --- | --- | --- |
| 14 | 51 | 598 | 1.0 |
| 15 | 43 | 597 | 2.1 |

Each of luminescence states of the organic EL devices was similar to that based on photoluminescence in the case where each of the luminescence materials was dissolved in toluene.

Accordingly, luminescence from these organic EL devices was found to be resulting from the respective metal coordination compounds of formulas 51 and 43.

Further, as apparent from the above results, the metal coordination compound of formula 43 effectively improved the luminescence efficiency when compared with the metal coordination compound of formula 51.

In these metal coordination compounds of formulas 43 and 51, the luminescent ligand was the benzothienylpyridine ligand and thus the luminescence efficiency was found to be dependent upon the number of the benzothienylpyridine ligand.

According to these examples (Examples 14 and 15), it was confirmed that a lesser number of the benzothienylpyridine ligand (constituting the metal coordination compound of formula 43) as the luminescent ligand was more effective in improving the luminescence efficiency.

As described hereinabove, according to the present invention, it is possible to provide a metal coordination compound of the formula (1) suitable as a luminescent material for broader wavelength range luminescence of an organic EL device and exhibiting a higher phosphorescence yield and a shorter phosphorescence life (time). An organic luminescence device (EL device) using the metal coordination compound according to the present invention stably exhibits high-efficiency luminescence.

What is claimed is:

1. A metal coordination compound represented by the following formula:

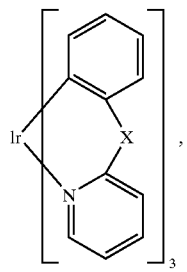

wherein X is C=O.

2. An organic luminescence device comprising:

at least a pair of electrodes; and an organic layer, which is disposed between the pair of electrodes and which comprises a metal coordination compound according to claim 1.

3. A display apparatus comprising a display portion, which comprises an organic luminescence device according to claim 2.

* * * * *

UNITED STATES PATENT AND TRADEMARK OFFICE
CERTIFICATE OF CORRECTION

PATENT NO. : 6,991,857 B2
APPLICATION NO. : 09/995608
DATED : January 31, 2006
INVENTOR(S) : Akira Tsuboyama et al.

It is certified that error appears in the above-identified patent and that said Letters Patent is hereby corrected as shown below:

ON THE TITLE PAGE [56] RERENCES CITED:

U.S. Patent Documents, "12/1997 Börner et al." should read
--12/1997 Börner--; and
Other Publications, (page 2 column 2)
after "Sergey" (first occurrence): "Apr. 15, 2001." should read --Apr. 13, 2001.-- and "4304-2312" should read --2304-2312--;
after "Sergey" (second occurrence): "Pt(11)" should read --Pt(II)-- and "(111)" should read --(III)--;
after C.H. Chen: "no month." should read --(no month).--;
after K.A. King: "J. Am. Chem. Soc." should be italicized; and
after Maestri: "Luninescence of Cyco-" should read --Luminescence of Cyclo- --.

COLUMN 9:

Line 38, "is" should read --are--;
Line 43, "Electrophotophorescent" should read --Electrophosphorescent--; and
Line 66, "different two" should read --two different--.

COLUMN 10:

Line 45, "H" should be deleted.

COLUMN 15:

Line 21, "to" should be deleted;
Line 36, "benzothienyl-pyridine" should read --benzothienylpyridine--;
Line 42, "zothienyl-pyridine" should read --zothienylpyridine--; and
Line 54, "benzothienyl-pryidine" should read --benzothienylpyridine--.

COLUMN 16:

Line 21, "benzo-thienylpyridine" should read --benzothienylpyridine--.

UNITED STATES PATENT AND TRADEMARK OFFICE
CERTIFICATE OF CORRECTION

PATENT NO. : 6,991,857 B2
APPLICATION NO. : 09/995608
DATED : January 31, 2006
INVENTOR(S) : Akira Tsuboyama et al.

It is certified that error appears in the above-identified patent and that said Letters Patent is hereby corrected as shown below:

COLUMN 19:

Lines 14-25, " " should read -- --.

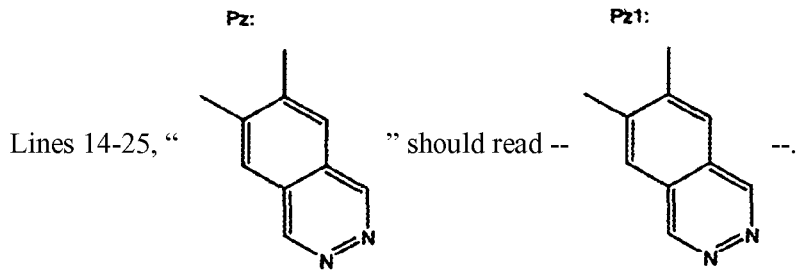

COLUMN 20:

Lines 3-10, " " should read -- --.

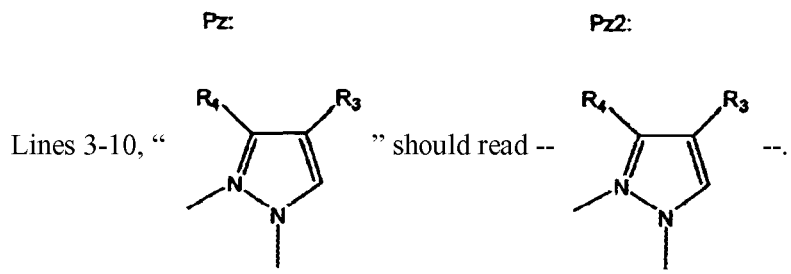

Line 35, " " should read -- --.

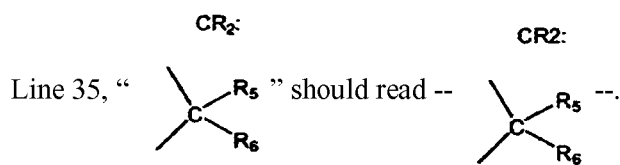

COLUMN 23:

Table 1, Nos. 81 through 100: "Pr1" should read --Py1--; and
Table 1, Nos. 121 through 136: "Pr2" should read --Py2--.

UNITED STATES PATENT AND TRADEMARK OFFICE
CERTIFICATE OF CORRECTION

PATENT NO.       : 6,991,857 B2
APPLICATION NO.  : 09/995608
DATED            : January 31, 2006
INVENTOR(S)      : Akira Tsuboyama et al.

It is certified that error appears in the above-identified patent and that said Letters Patent is hereby corrected as shown below:

COLUMN 25:

Table 1, Nos. 137 through 140: "Pr2" should read --Py2--; and
  Table 1, No. 194, after "Pr NR Cnl": " H " should read -- – --.

COLUMN 29:

Table 1, No. 292, after "Pr" (second occurrence): "Qx1" should read --Qz1--;
  Table 1, No. 293, after "Pr" (second occurrence): "Qx2" should read --Qz2--; and
  Table 1, No. 327, after "Pr": "Tn1" should read --Tn2--.

COLUMN 31:

Table 1, No. 363, after "Py2 Qzl": " H – " shuld read -- – H --; and
  Table 1, No. 406, after "Ir 2 1": "pa" should read --Pa--.

COLUMN 33:

Table 1, No. 481, after "Pr" (second occurrence): "Qn2" should read --Cn2--; and
  Table 1, No. 493, after "Pr" (second occurrence): "Cr1" should read --Cn1--.

UNITED STATES PATENT AND TRADEMARK OFFICE
CERTIFICATE OF CORRECTION

PATENT NO.        : 6,991,857 B2                                    Page 4 of 5
APPLICATION NO. : 09/995608
DATED             : January 31, 2006
INVENTOR(S)       : Akira Tsuboyama et al.

It is certified that error appears in the above-identified patent and that said Letters Patent is hereby corrected as shown below:

COLUMN 43:

Lines 50-65, " 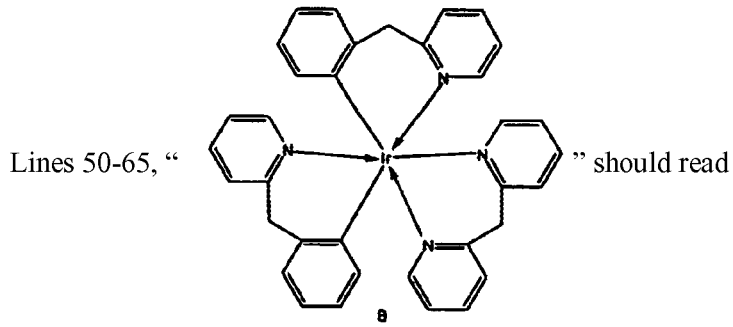 " should read

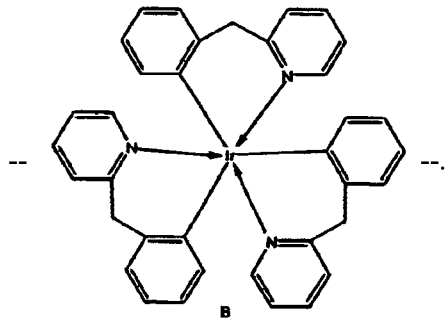

-- ... --.

COLUMN 44:

Line 6, "acetyl-acetonate" should read --acetylacetonate--.

UNITED STATES PATENT AND TRADEMARK OFFICE
CERTIFICATE OF CORRECTION

PATENT NO. : 6,991,857 B2
APPLICATION NO. : 09/995608
DATED : January 31, 2006
INVENTOR(S) : Akira Tsuboyama et al.

It is certified that error appears in the above-identified patent and that said Letters Patent is hereby corrected as shown below:

COLUMN 46:

Line 18, "12.6 g o" should read --12.6 g of--;
Line 25, " ⎯⎯ " should read -- ⎯⎯ --; and
Line 58, "followed" should read --followed by--.

Signed and Sealed this

Seventh Day of November, 2006

JON W. DUDAS
*Director of the United States Patent and Trademark Office*